(12) United States Patent
Goldberg et al.

(10) Patent No.: US 11,571,310 B2
(45) Date of Patent: Feb. 7, 2023

(54) STEMMED IMPLANT

(71) Applicant: CATALYST ORTHOSCIENCE INC., Naples, FL (US)

(72) Inventors: Steven Scott Goldberg, Naples, FL (US); Dale Davison, Naples, FL (US); Ephraim Akyuz, Salt Lake City, UT (US); Daniel J. Triplett, Providence, UT (US); Zachary R. Leitze, St. George, UT (US); John G. Costouros, Hillsborough, CA (US)

(73) Assignee: Catalyst Orthoscience Inc., Naples, FL (US)

( * ) Notice: Subject to any disclaimer, the term of this patent is extended or adjusted under 35 U.S.C. 154(b) by 63 days.

(21) Appl. No.: 16/838,727

(22) Filed: Apr. 2, 2020

(65) Prior Publication Data

US 2020/0315808 A1 Oct. 8, 2020

Related U.S. Application Data

(60) Provisional application No. 62/828,799, filed on Apr. 3, 2019.

(51) Int. Cl.
*A61F 2/40* (2006.01)
*A61F 2/30* (2006.01)

(52) U.S. Cl.
CPC .......... *A61F 2/4014* (2013.01); *A61F 2/4059* (2013.01); *A61F 2002/30181* (2013.01); *A61F 2002/30879* (2013.01); *A61F 2002/4029* (2013.01); *A61F 2002/4051* (2013.01); *A61F 2002/4062* (2013.01); *A61F 2230/0067* (2013.01); *A61F 2230/0069* (2013.01); *A61F 2230/0071* (2013.01)

(58) Field of Classification Search
CPC .. A61F 2/4014; A61F 2/40; A61F 2/32; A61F 2/367; A61F 2/3609; A61F 2002/4062; A61F 2002/4022; A61F 2002/4029; A61F 2002/3613; A61F 2002/3615; A61F 2002/3625; A61F 2002/3627; A61F 2002/3647; A61F 2002/30181; A61F 2230/006; A61F 2/4059; A61F 2002/407; A61F 2002/4077
See application file for complete search history.

(56) References Cited

U.S. PATENT DOCUMENTS

| | | |
|---|---|---|
| 3,842,442 A | 10/1974 | Kolbel |
| 3,916,451 A | 11/1975 | Buechel |
| 3,978,528 A | 9/1976 | Crep |
| 4,003,095 A | 1/1977 | Gristina |

(Continued)

FOREIGN PATENT DOCUMENTS

EP 2083759 B1 9/2015

*Primary Examiner* — Suba Ganesan
(74) *Attorney, Agent, or Firm* — David Meibos; Maywood IP Law

(57) ABSTRACT

A stemmed implant comprises a proximal body with a distal shaft extending from the proximal body. The proximal body exterior may be spherical, conical, cylindrical, or another surface of revolution. The distal shaft comprises multiple longitudinal ridges which may originate from the proximal body as separate columns, or which may merge together. The distal shaft and/or the ridges may become narrower as they extend away from the proximal body.

24 Claims, 17 Drawing Sheets

(56) References Cited

U.S. PATENT DOCUMENTS

| | | | | |
|---|---|---|---|---|
| 4,206,517 | A | 6/1980 | Pappas | |
| 4,532,661 | A | 8/1985 | Halpern | |
| 4,693,723 | A | 9/1987 | Gabard | |
| 4,919,669 | A | 4/1990 | Lannelongue | |
| 5,489,309 | A | 2/1996 | Lackey | |
| 5,549,682 | A | 8/1996 | Roy | |
| 5,723,018 | A | 3/1998 | Cyprien | |
| 5,944,758 | A | 8/1999 | Mansat | |
| 5,961,555 | A | 10/1999 | Huebner | |
| 6,045,582 | A | 4/2000 | Prybyla | |
| 6,171,341 | B1 | 1/2001 | Boileau | |
| 6,228,120 | B1 | 5/2001 | Leonard | |
| 6,398,812 | B1 | 6/2002 | Masini | |
| 6,508,840 | B1 | 1/2003 | Rockwood, Jr. | |
| 6,679,916 | B1 | 1/2004 | Frankle | |
| 6,761,740 | B2 | 7/2004 | Tornier | |
| 6,783,549 | B1 | 8/2004 | Stone | |
| 6,790,234 | B1 | 9/2004 | Frankle | |
| 6,953,478 | B2 | 10/2005 | Bouttens | |
| 7,011,686 | B2 | 3/2006 | Ball | |
| 7,169,184 | B2 | 1/2007 | Dalla Pria | |
| 7,175,663 | B1 | 2/2007 | Stone | |
| 7,241,314 | B1 | 7/2007 | Winslow | |
| 7,255,717 | B2 | 8/2007 | Park | |
| 7,309,360 | B2 | 12/2007 | Tornier | |
| 7,462,197 | B2 | 12/2008 | Tornier | |
| 7,585,327 | B2 | 9/2009 | Winslow | |
| 7,621,961 | B2 | 11/2009 | Stone | |
| 7,670,382 | B2 | 3/2010 | Parrott | |
| 7,678,150 | B2 | 3/2010 | Tornier | |
| 7,854,768 | B2 | 12/2010 | Wiley | |
| 7,959,680 | B2 | 6/2011 | Stone | |
| 8,062,376 | B2 | 11/2011 | Shultz | |
| 8,070,820 | B2 | 12/2011 | Winslow | |
| 8,157,866 | B2 | 4/2012 | Winslow | |
| 8,241,366 | B2 | 8/2012 | Roche | |
| 8,246,687 | B2 | 8/2012 | Katrana | |
| 8,277,512 | B2 | 10/2012 | Parrott | |
| 8,317,871 | B2 | 11/2012 | Stone | |
| 8,337,563 | B2 | 12/2012 | Roche | |
| 8,449,617 | B1 | 5/2013 | McDaniel | |
| 8,454,702 | B2 | 6/2013 | Smits | |
| 8,454,703 | B2 | 6/2013 | Linares | |
| 8,512,410 | B2 | 8/2013 | Metcalfe | |
| 8,591,591 | B2 | 11/2013 | Winslow | |
| 8,632,597 | B2 | 1/2014 | Lappin | |
| 8,632,598 | B2 | 1/2014 | McDaniel | |
| 8,663,333 | B2 | 3/2014 | Metcalfe | |
| 8,663,335 | B2 | 3/2014 | Katrana | |
| 8,690,952 | B2 | 4/2014 | Dallmann | |
| 8,702,800 | B2 | 4/2014 | Linares | |
| 8,721,728 | B2 | 5/2014 | Winslow | |
| 8,814,941 | B2 | 8/2014 | Katrana | |
| 8,840,672 | B2 | 9/2014 | Winslow | |
| 8,845,743 | B2 | 9/2014 | Termanini | |
| 8,864,834 | B2 | 10/2014 | Boileau | |
| 8,870,962 | B2 | 10/2014 | Roche | |
| 8,888,855 | B2 | 11/2014 | Roche | |
| 8,936,646 | B2 | 1/2015 | Parrott | |
| 8,940,054 | B2 | 1/2015 | Wiley | |
| 8,945,229 | B2 | 2/2015 | Lappin | |
| 8,945,234 | B2 | 2/2015 | Humphrey | |
| 8,968,410 | B2 | 3/2015 | Veronesi | |
| 8,974,536 | B2 | 3/2015 | Walch | |
| 8,998,994 | B2 | 4/2015 | Winslow | |
| D735,338 | S | 7/2015 | Goldberg | |
| 9,119,724 | B2 | 9/2015 | Termanini | |
| D746,989 | S | 1/2016 | Goldberg | |
| 9,232,955 | B2 | 1/2016 | Bonin, Jr. | |
| 9,233,003 | B2 | 1/2016 | Roche | |
| 9,278,005 | B2 | 3/2016 | Smits | |
| 9,283,075 | B2 | 3/2016 | Wiley | |
| 9,283,083 | B2 | 3/2016 | Winslow | |
| 9,289,306 | B2 | 3/2016 | Goldberg | |
| 9,314,344 | B2 | 4/2016 | Parrott | |
| 9,498,344 | B2 | 11/2016 | Hodorek | |
| 9,504,581 | B2 | 11/2016 | Parrott | |
| 9,510,952 | B2 | 12/2016 | Muir | |
| 9,522,067 | B2 | 12/2016 | Frankle | |
| 9,597,203 | B2 | 3/2017 | Emerick | |
| 9,622,869 | B2 | 4/2017 | Nerot | |
| 9,763,797 | B2 | 9/2017 | Hopkins | |
| 9,763,799 | B2 | 9/2017 | Smits | |
| 9,770,334 | B2 | 9/2017 | Wiley | |
| 9,814,587 | B2 | 11/2017 | Goldberg | |
| 10,172,714 | B2 | 1/2019 | Hatzidakis | |
| 10,265,185 | B2 | 4/2019 | Goldberg | |
| 10,433,967 | B2 * | 10/2019 | Deransart | A61F 2/4014 |
| 2003/0097183 | A1 | 5/2003 | Rauscher | |
| 2004/0220674 | A1 | 11/2004 | Pria | |
| 2004/0225367 | A1 | 11/2004 | Glien | |
| 2005/0261775 | A1 | 11/2005 | Baum | |
| 2005/0278030 | A1 | 12/2005 | Tornier | |
| 2006/0009852 | A1 | 1/2006 | Winslow | |
| 2006/0069445 | A1 | 3/2006 | Ondrla | |
| 2008/0228281 | A1 | 9/2008 | Forrer | |
| 2008/0234829 | A1 * | 9/2008 | Mutchler | A61F 2/4014 |
| | | | | 623/19.14 |
| 2009/0043397 | A1 | 2/2009 | Park | |
| 2009/0099662 | A1 | 4/2009 | Splieth | |
| 2009/0149961 | A1 | 6/2009 | Dallmann | |
| 2009/0171462 | A1 * | 7/2009 | Poncet | A61F 2/4059 |
| | | | | 623/19.12 |
| 2009/0306782 | A1 | 12/2009 | Schwyzer | |
| 2010/0023068 | A1 | 1/2010 | Bouttens | |
| 2010/0049327 | A1 | 2/2010 | Isch | |
| 2010/0125336 | A1 | 5/2010 | Johnson | |
| 2010/0161066 | A1 | 6/2010 | Iannotti | |
| 2010/0217399 | A1 | 8/2010 | Groh | |
| 2010/0222889 | A1 | 9/2010 | Howling | |
| 2011/0029089 | A1 | 2/2011 | Giuliani | |
| 2011/0060417 | A1 | 3/2011 | Simmen | |
| 2011/0106266 | A1 | 5/2011 | Schwyzer | |
| 2011/0288650 | A1 | 11/2011 | Ries | |
| 2012/0130500 | A1 | 5/2012 | Maroney | |
| 2012/0191205 | A1 | 7/2012 | Bojarski | |
| 2012/0209392 | A1 | 8/2012 | Angibaud | |
| 2012/0253467 | A1 | 10/2012 | Frankle | |
| 2012/0271425 | A1 | 10/2012 | Maurer | |
| 2012/0330428 | A1 | 12/2012 | Splieth | |
| 2013/0060341 | A1 | 3/2013 | Tornier | |
| 2013/0245775 | A1 | 9/2013 | Metcalfe | |
| 2013/0261751 | A1 | 10/2013 | Lappin | |
| 2014/0156011 | A1 | 6/2014 | Termanini | |
| 2014/0228961 | A1 | 8/2014 | Linares | |
| 2014/0236303 | A1 | 8/2014 | Maurer | |
| 2014/0277520 | A1 | 9/2014 | Chavarria | |
| 2014/0379088 | A1 | 12/2014 | Katrana | |
| 2015/0012104 | A1 | 1/2015 | Boileau | |
| 2015/0018959 | A1 | 1/2015 | Tornier | |
| 2015/0088261 | A1 | 3/2015 | Lappin | |
| 2015/0088262 | A1 | 3/2015 | Lappin | |
| 2015/0134066 | A1 | 5/2015 | Bachmaier | |
| 2015/0173906 | A1 | 6/2015 | Winslow | |
| 2015/0250601 | A1 | 9/2015 | Humphrey | |
| 2015/0250602 | A1 | 9/2015 | Sikora | |
| 2015/0335440 | A1 | 11/2015 | Linares | |
| 2016/0120555 | A1 | 5/2016 | Bonin, Jr. | |
| 2016/0262902 | A1 | 9/2016 | Winslow | |
| 2016/0310285 | A1 | 10/2016 | Kovacs | |
| 2016/0374815 | A1 | 12/2016 | Siccardi | |
| 2017/0007330 | A1 | 1/2017 | Britton | |
| 2017/0042687 | A1 | 2/2017 | Boileau | |
| 2017/0049573 | A1 | 2/2017 | Hodorek | |
| 2017/0105843 | A1 | 4/2017 | Britton | |
| 2017/0181860 | A1 | 6/2017 | Nerot | |
| 2017/0202673 | A1 | 7/2017 | Winslow | |
| 2017/0273806 | A1 | 9/2017 | Cardon | |
| 2017/0325962 | A1 | 11/2017 | Wiley | |
| 2017/0340449 | A1 * | 11/2017 | Deransart | A61F 2/4014 |
| 2018/0104073 | A1 | 4/2018 | Long | |
| 2019/0046326 | A1 | 2/2019 | Ball | |

(56) References Cited

U.S. PATENT DOCUMENTS

| | | |
|---|---|---|
| 2020/0214846 A1 | 7/2020 | Perego et al. |
| 2021/0038401 A1* | 2/2021 | Ball .................. A61F 2/4081 |

* cited by examiner

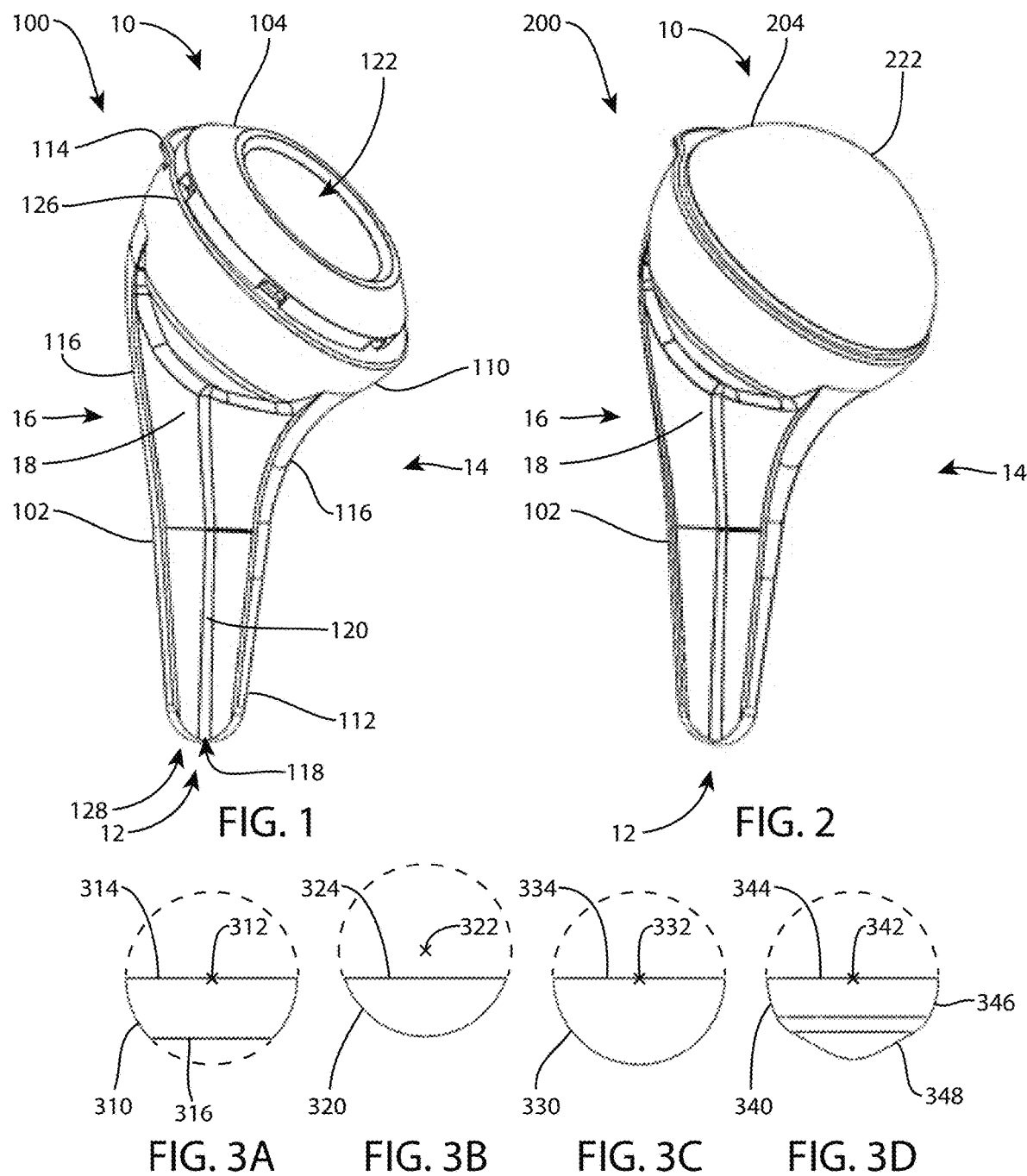

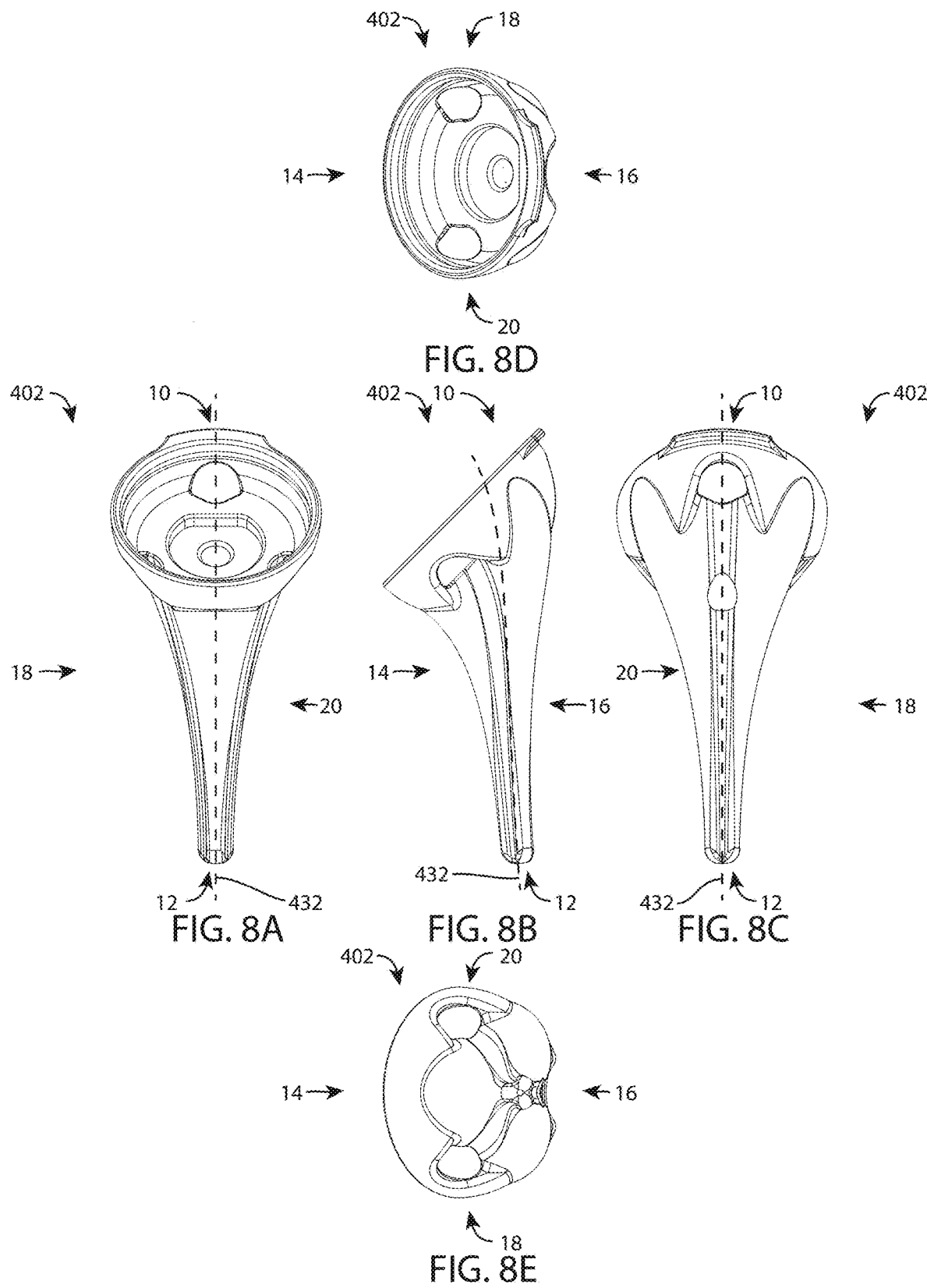

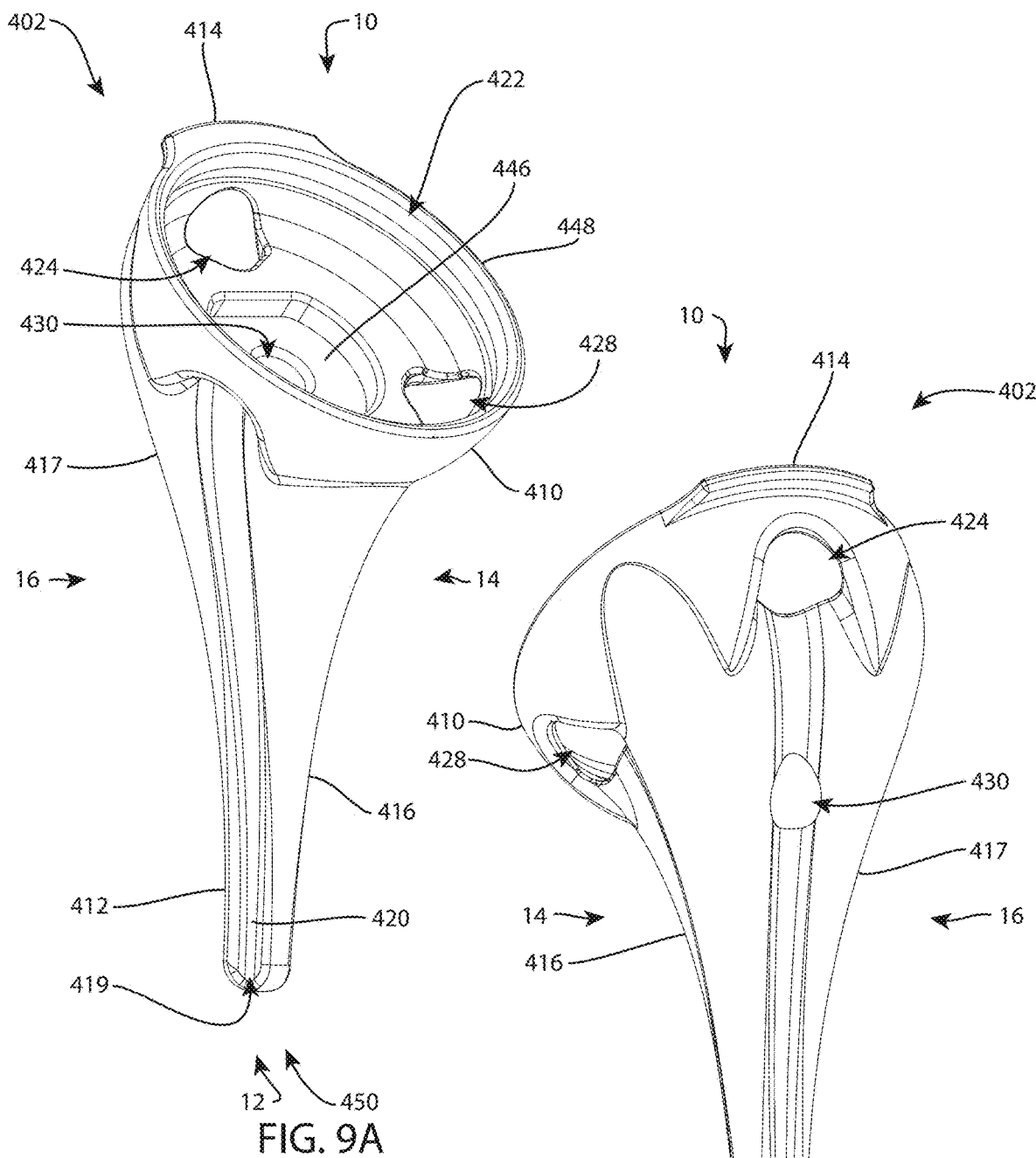
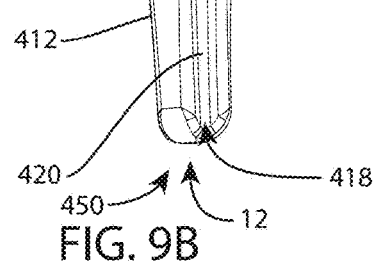

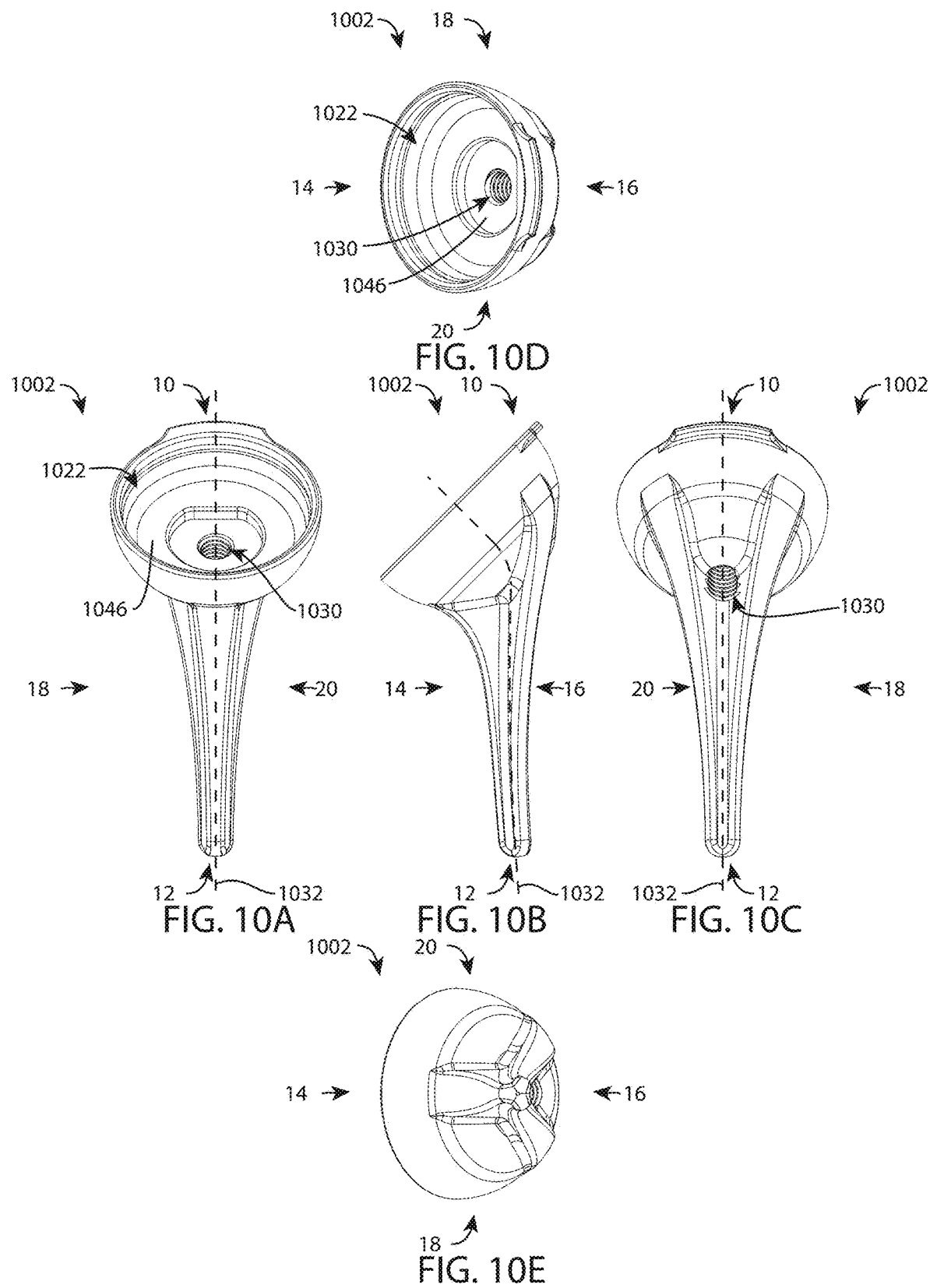

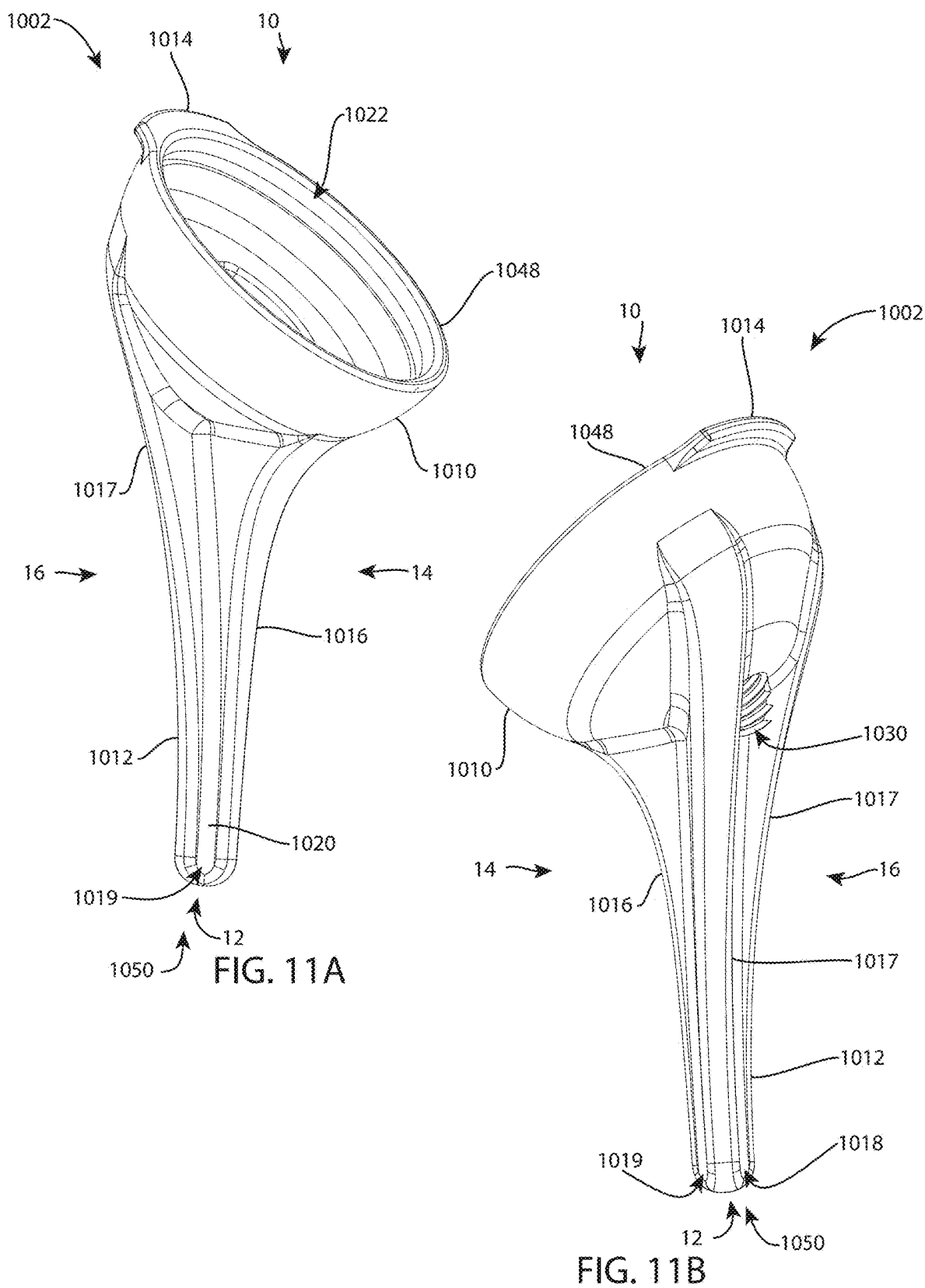

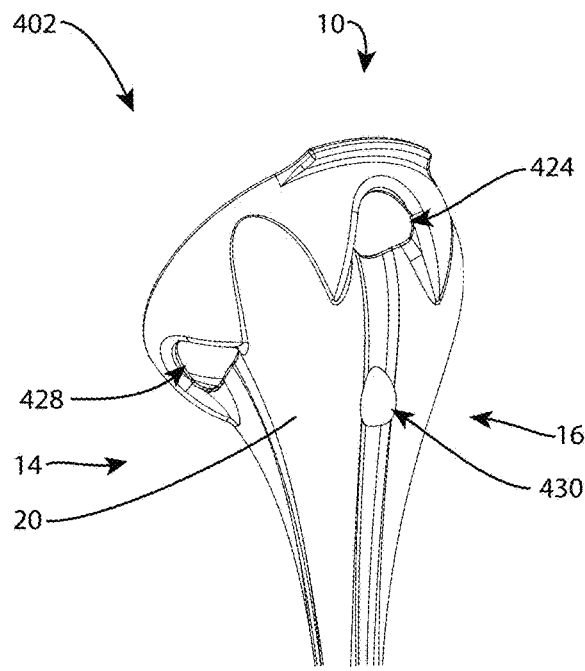
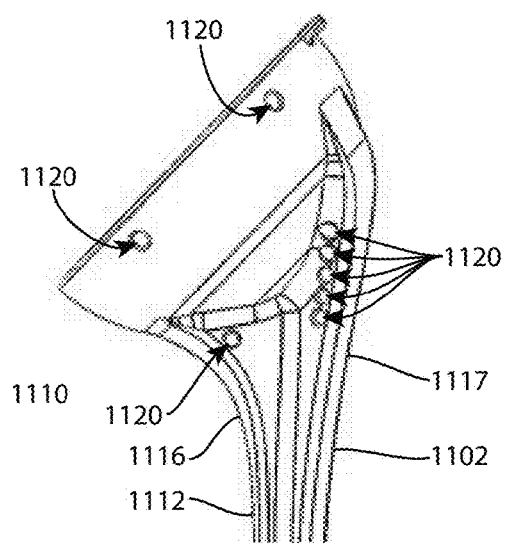
FIG. 13                FIG. 14
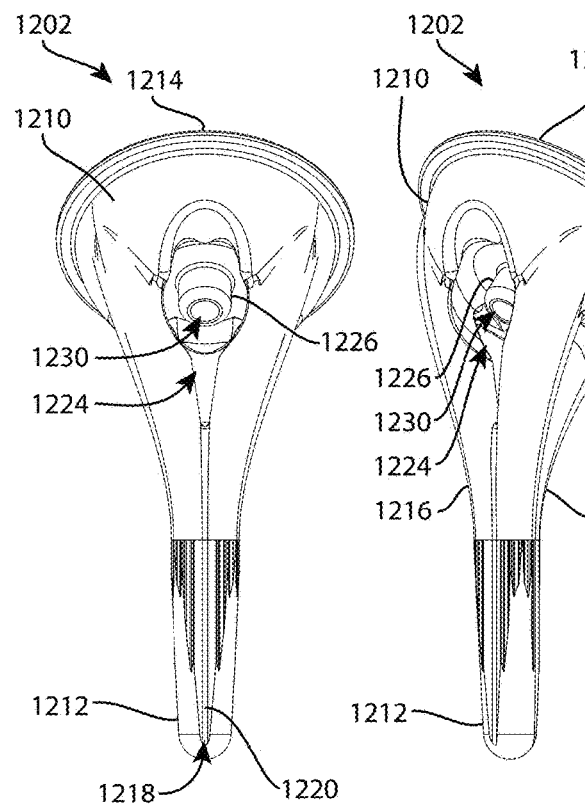
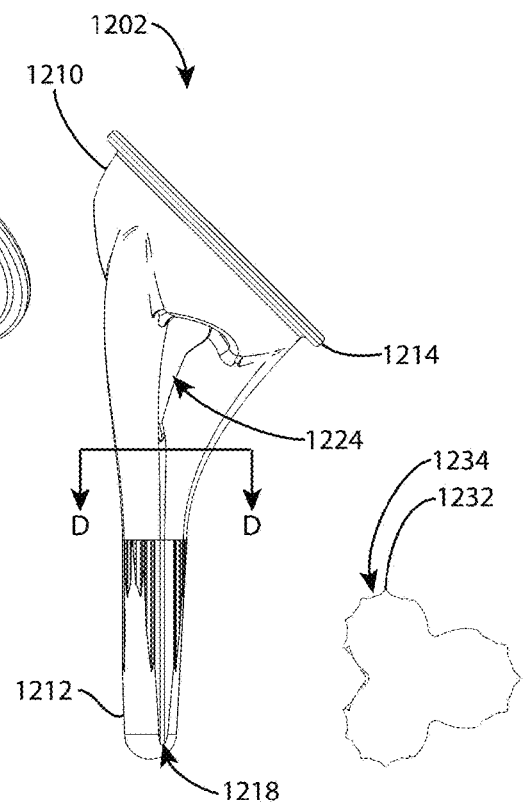
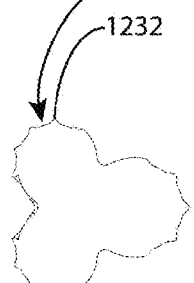
FIG. 15A     FIG. 15B     FIG. 15C     FIG. 15D

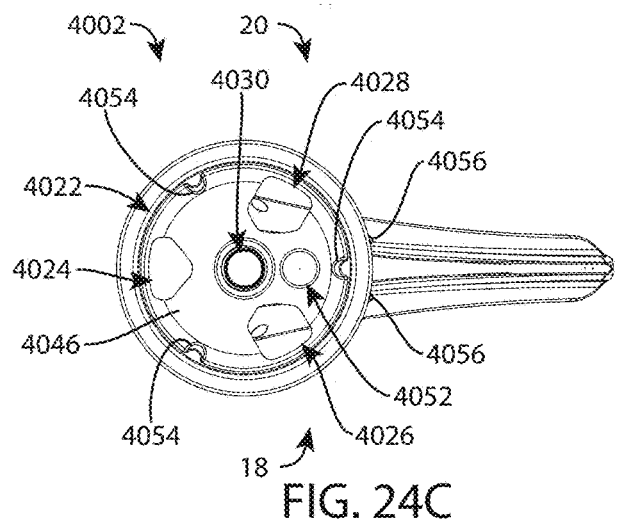
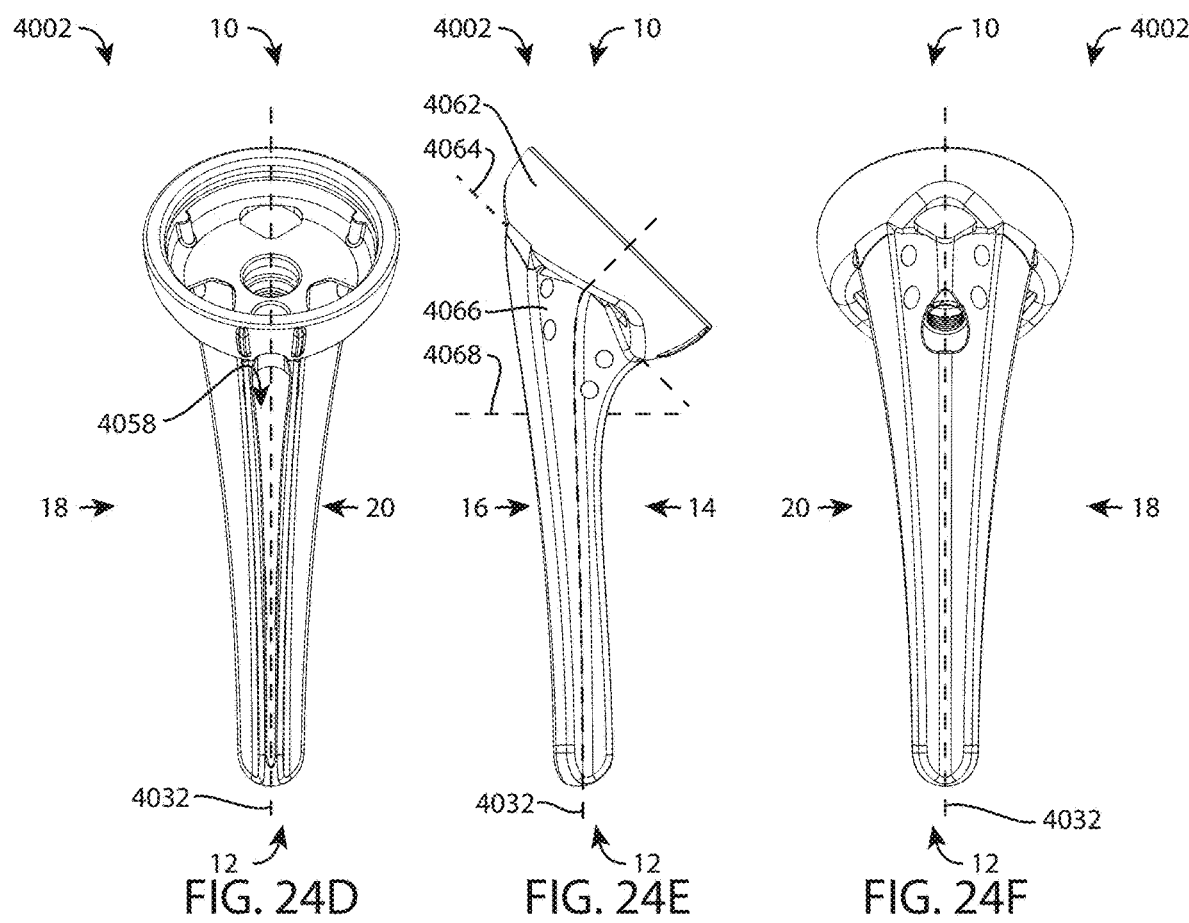

STEMMED IMPLANT

CROSS-REFERENCE TO RELATED APPLICATIONS

The present application claims the benefit of:

U.S. Provisional Application Ser. No. 62/828,799, filed on Apr. 3, 2019, entitled STEMMED IMPLANT.

The foregoing is incorporated by reference as though set forth herein in its entirety.

TECHNICAL FIELD

The present disclosure relates to joint arthroplasty implants. More specifically, the present disclosure relates to implants with a stemmed portion that extends into the metaphysis and optionally into the diaphysis of a long bone. While the present disclosure is made in the context of a humeral implant for shoulder arthroplasty, the disclosed principles are applicable to implants for other locations.

BACKGROUND

Joint arthroplasty procedures are conducted to restore the function of an unhealthy joint. Typically, these procedures involve replacing the unhealthy natural articulating surfaces of the joint with artificial articulating surfaces. The new artificial articulating surfaces are typically anchored into the adjacent bones to maintain long term stability.

In shoulder arthroplasty, a humeral implant is attached to the humerus and a glenoid implant is attached to the glenoid or scapula. There are two different main categories of shoulder arthroplasty: anatomic and reverse. In an anatomic procedure, the implant designs are intended to replicate the natural anatomy. The humeral head is replaced with a similarly shaped convex hemispherical surface, while the glenoid is replaced with a shallow concave socket. In a reverse procedure, the natural ball and socket is reversed. The humeral head is replaced with a socket fixed to the humerus and the glenoid is replaced with a ball (or glenosphere) fixed to the scapula.

Regardless of the type of procedure, fixation of the humeral component into the humerus typically involves an implant with a stemmed portion that extends into the metaphysis and optionally into the diaphysis of the humerus.

The goals of these implants are to preserve as much native bone as possible, maximize the mechanical stability of the implant, and allow for more physiological loading of the bone to preserve the long term fixation of the implant.

These implants may be used in various surgical procedures that utilize a stemmed fixation that requires rotational stability. The present disclosure is made in the context of a humeral implant for shoulder arthroplasty. Other applications may include a femoral implant for hip or knee arthroplasty, a tibial implant for knee or ankle arthroplasty, or implants for the elbow, wrist, hand, and foot.

The implants disclosed herein emphasize metaphyseal fit and fill. The stem profiles are medially biased. The proximal bodies of the stems are positionable within a prepared proximal humerus so that the proximal body rim is aligned with the humeral osteotomy, while the distal shaft enables such positioning without interfering with final stem seating. Optional fixation elements may extend through the proximal bodies from inside-out. The stems include ridges and grooves to enhance rotational stability of the implants in bone by fitting within non-circular cortical walls. Rounded and rectangular ridges are disclosed, preferably in groups of three to seven, more preferably in odd-numbered groups of three or five. Surface structures may be provided on the stems for immediate mechanical fixation and long-term bone ingrowth.

SUMMARY

The various systems and methods of the present technology have been developed in response to the present state of the art, and in particular, in response to the problems and needs in the art that have not yet been fully solved by currently available stemmed implants. The systems and methods of the present technology may provide greater bone preservation, greater initial mechanical stability of the implant, and more physiological loading of the supporting bone to provide greater long-term implant fixation.

To achieve the foregoing, and in accordance with the technology as embodied and broadly described herein, an aspect of the technology features a stem component for implantation in at least a metaphysis of a long bone, the stem component including: a body portion including an exterior, wherein the exterior includes a portion of a sphere; and a shaft portion integrally formed with the body portion and extending outwardly from the exterior of the body portion along a longitudinal shaft centerline, wherein the shaft portion includes at least three longitudinal ridges arranged around the shaft centerline, wherein each ridge extends radially away from the shaft centerline a first distance near the body portion and a second distance farther from the body portion, wherein the second distance is less than the first distance.

Embodiments of this aspect of the technology may include one or more of the following attributes. The body portion includes an interior socket including a plurality of noncircular holes arranged around a center of the socket and extending through the body portion. The shape of each noncircular hole is based upon the shapes of the corresponding ridges in the vicinity of that noncircular hole. The body portion includes an interior socket including a central hole in a bottom surface of the socket and extending through the body portion. The shaft portion includes a cross-sectional shape including a Y-shape. Each ridge includes a first transverse width near the body portion and a second transverse width farther from the body portion, wherein the second transverse width is less than the first transverse width. Each ridge is separate from the other ridges near the body portion, wherein the ridges merge together farther from the body portion.

In another aspect of the technology, a stem component for implantation in at least a metaphysis of a long bone includes: a body portion including an exterior, wherein the exterior includes a portion of a sphere; and a shaft portion integrally formed with the body portion and extending outwardly from the exterior of the body portion along a longitudinal shaft centerline, wherein the shaft portion includes a cross-sectional shape including at least three lobes, wherein each lobe extends radially away from the shaft centerline, wherein the shaft portion includes a first cross-sectional overall outer diameter near the body portion and a second cross-sectional overall outer diameter farther from the body portion, wherein the second cross-sectional overall outer diameter is less than the first cross-sectional overall outer diameter.

Embodiments of this aspect of the technology may include one or more of the following attributes. The body portion includes an interior socket including a plurality of noncircular holes arranged around a center of the socket and extending through the body portion. The shape of each noncircular hole is based upon the shapes of the corresponding lobes in the vicinity of that noncircular hole. The body portion includes an interior socket including a central hole in a bottom surface of the socket and extending through the body portion. The shaft portion includes a cross-sectional shape including a Y-shape. Each lobe includes a first transverse width near the body portion and a second transverse width farther from the body portion, wherein the second transverse width is less than the first transverse width.

In yet another aspect of the technology, a stem component for implantation in at least a metaphysis of a long bone includes: a body portion including an exterior, wherein the exterior includes a portion of a sphere; and a shaft portion integrally formed with the body portion and extending outwardly from the exterior of the body portion along a longitudinal shaft centerline, wherein the shaft portion includes at least three longitudinal columns arranged around the shaft centerline, wherein each column is separate from the remaining columns near the body portion, wherein the columns merge together farther from the body portion.

Embodiments of this aspect of the technology may include one or more of the following attributes. The body portion includes an interior socket including a plurality of noncircular holes arranged around a center of the socket and extending through the body portion. The shape of each noncircular hole is based upon the shapes of the corresponding columns in the vicinity of that noncircular hole. The body portion includes an interior socket including a central hole in a bottom surface of the socket and extending through the body portion. The body portion includes an interior socket including a hole extending through the body portion, wherein the stem portion includes a cavity near the body portion, wherein the cavity is surrounded by the columns, wherein the hole and the cavity are open to each other. The shaft portion includes a first cross-sectional overall outer diameter near the body portion and a second cross-sectional overall outer diameter farther from the body portion, wherein the second cross-sectional overall outer diameter is less than the first cross-sectional overall outer diameter. Each column includes a first transverse width near the body portion and a second transverse width farther from the body portion, wherein the second transverse width is less than the first transverse width.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 1 is an oblique view of a humeral implant with a humeral stem and a concave articular component;

FIG. 2 is an oblique view of another humeral implant with the humeral stem of FIG. 1 and a convex articular component;

FIG. 3A is a side view of a proximal body of a humeral stem; FIG. 3B is a side view of another proximal body of a humeral stem; FIG. 3C is a side view of yet another proximal body of a humeral stem; and FIG. 3D is a side view of yet another proximal body of a humeral stem;

FIG. 8A is a medial view of the humeral stem of FIG. 4; FIG. 8B is a posterior view of the humeral stem of FIG. 4; FIG. 8C is a lateral view of the humeral stem of FIG. 4; FIG. 8D is a superior view of the humeral stem of FIG. 4; and FIG. 8E is an inferior view of the humeral stem of FIG. 4;

FIG. 9A is an oblique view of the humeral stem of FIG. 4; and FIG. 9B is another oblique view of the humeral stem of FIG. 4 from a different direction;

FIG. 10A is a medial view of yet another humeral stem; FIG. 10B is a posterior view of the humeral stem of FIG. 10A; FIG. 10C is a lateral view of the humeral stem of FIG. 10A; FIG. 10D is a superior view of the humeral stem of FIG. 10A; and FIG. 10E is an inferior view of the humeral stem of FIG. 10A;

FIG. 11A is an oblique view of the humeral stem of FIG. 10A and FIG. 11B is another oblique view of the humeral stem of FIG. 10A from a different direction;

FIG. 13 is an oblique detail view of a portion of the humeral stem of FIG. 4;

FIG. 14 is a posterior detail view of a portion of yet another humeral stem;

FIG. 15A is a lateral view of yet another humeral stem; FIG. 15B is an oblique view of the humeral stem of FIG. 15A; FIG. 15C is an anterior view of the humeral stem of FIG. 15A; and FIG. 15D is a cross-sectional view taken along section line D-D of FIG. 15C;

FIG. 24C is a view perpendicular to a bottom surface of a socket of the humeral stem of FIG. 24A; FIG. 24D is a medial view of the humeral stem of FIG. 24A; FIG. 24E is an anterior view of the humeral stem of FIG. 24A; and FIG. 24F is a lateral view of the humeral stem of FIG. 24A.

DETAILED DESCRIPTION

Figure 4:
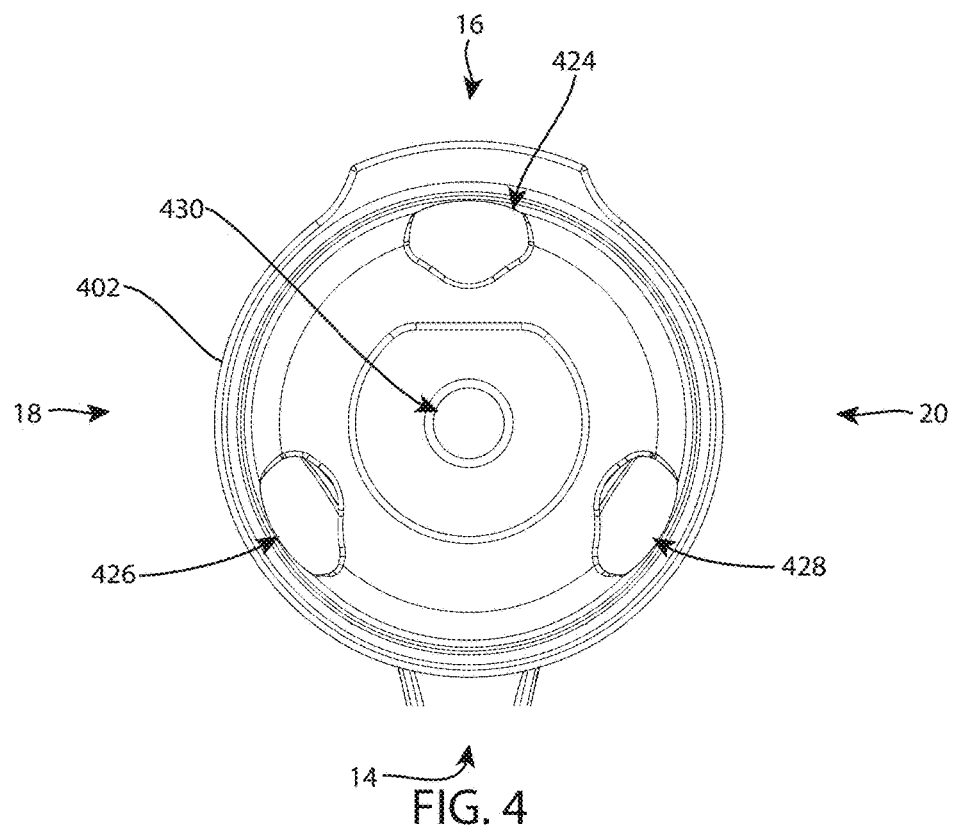
FIG. 4 is a view perpendicular to a bottom surface of a socket of another humeral stem.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

In this specification, standard shoulder anatomical terms are employed with their ordinary and customary meanings.

Referring to FIG. 1, a humeral implant 100 includes a humeral stem 102 and may include a concave articular component 104 for a reverse shoulder procedure. Humeral implant 100, humeral stem 102, and concave articular component 104 have a proximal end 10, a distal end 12, a medial side 14, a lateral side 16, an anterior side 18, and a posterior side 20. These six directional terms apply to all of the implants, stems, and articular components discussed below, and to their features.

The humeral stem 102 includes a proximal body 110 and a distal shaft 112. In an embodiment, the distal shaft 112 may be integrally formed with the proximal body 110 to form a one-piece humeral stem 102. The proximal body 110 may have a generally hemispherical exterior shape and an interior socket (not visible) with features shaped to receive an articular component, such as concave articular component 104. These features of the interior socket may be referred to as an articular component interconnection or interface. A partial or continuous flange 114 may extend medially, anteriorly, laterally, and/or posteriorly from the proximal end 10 of the proximal body 110, for example, a flange may extend from a proximal rim 126 of the proximal body 110. A lateral partial flange 114 is shown. The distal shaft 112 may extend distally from the exterior of the proximal body 110 to terminate at a free end 128 at the distal end 12. The distal shaft 112 may start out the same size or similar in size to the proximal body 110 and may become smaller farther from the proximal body, towards the distal end 12. The distal shaft 112 may have a larger outer diameter near the proximal body 110 and a smaller outer diameter farther from the proximal body, near the free end 128. The distal shaft 112 may include alternating longitudinal ridges 116 and grooves 118. This design includes three ridges 116 and three grooves 118, giving the distal shaft 112 a cross-sectional shape that may be described as tri-lobed, triangular, or Y-shaped. The ridges 116 may merge together to form a central longitudinal solid portion 120 of the distal shaft 112.

The concave articular component 104 includes an articular surface 122 for articulation with a glenoid implant (not shown), and a stem interconnection (not visible) with geometry shaped to connect to the articular component interconnection of the interior socket of the proximal body 110 of the humeral stem 102. The articular surface 122 in this example is concave hemispherical for articulation with a glenosphere.

Referring to FIG. 2, a humeral implant 200 includes the humeral stem 102 and may include a convex articular component 204, or ball, for an anatomical shoulder procedure.

The convex articular component 204 includes an articular surface 222 for articulation with a glenoid implant (not shown), and a stem interconnection (not visible) with geometry shaped to connect to the articular component interconnection of the interior socket of the proximal body 110 of the humeral stem 102. The stem interconnection may be identical to the interconnection portion 124 so that the convex articular component 204 is interchangeable with the concave articular component 104. The articular surface 222 in this example is convex hemispherical for articulation with a glenoid socket.

Referring to FIGS. 3A-D, the exteriors of four different humeral stem proximal bodies 310, 320, 330, 340 are shown in side views. Proximal body 310 is a spherical segment extending between a proximal plane 314 and a distal plane 316. The proximal plane passes through the spherical center point 312. Proximal body 320 is a spherical cap terminated by a proximal plane 324, which in this example is offset distally from the spherical center point 322. Proximal body 330 is another spherical cap terminated by a proximal plane 334 which passes through the spherical center point 332. Proximal body 330 is thus a true hemisphere. Proximal body 340 includes a spherical segment 346 terminated by a proximal plane 344 which passes through the spherical center point 342 and merges distally smoothly with a conical portion 348 having a rounded distal end. Any of the proximal bodies 310, 320, 330, 340 may be combined with the distal shaft 112, or the other distal shafts disclosed herein, in the design of a humeral stem. For example, the proximal body 110 of humeral stem 102 is illustrated to match proximal body 340 of FIG. 3D. Proximal bodies may have cylindrical, conical, or spherical shapes, or combinations of these shapes. Preferably, and by design, the proximal bodies disclosed herein are positionable within a prepared proximal humerus so that the proximal body rim is aligned with the humeral osteotomy, while the distal shaft is small enough to enable such positioning without interfering.

Referring to FIGS. 4, 8A-9B, and 12A-13, a humeral stem 402 includes a proximal body 410 and a distal shaft 412. In an embodiment, the distal shaft 412 may be integrally formed with the proximal body 410 to form a one-piece humeral stem 402.

The proximal body 410 may have a generally hemispherical exterior shape and an interior socket 422 with features shaped to receive an articular component, such as concave articular component 104 or convex articular component 204. The interior socket 422 may include a flat bottom surface 446 which may be parallel to a proximal rim 448 of the proximal body 410. The exterior of proximal body 410 may match one of the proximal bodies 310, 320, 330 of FIGS. 3A-C. The interior socket 422 may be referred to as an articular component interconnection or interface. A partial or continuous flange 414 may extend medially, anteriorly, laterally, and/or posteriorly from the proximal end 10 of the proximal body 410. A lateral partial flange 414 is shown extending from the rim 448. One or more holes may extend through the proximal body 410; four holes 424, 426, 428, 430 are shown. Holes 424, 426, 428 are shown with non-circular cross-sectional shapes which may be based upon the geometry of the corresponding ridges 416, 417 and grooves 418, 419 in the vicinity of the holes. Hole 430 is shown with a circular cross-sectional shape, seen best in FIG. 4. The holes 424, 426, 428, and/or 430 may provide means or openings for inserting instruments to aid in removing or extracting the implant from the bone after implantation. Holes 424, 426, 428 may enhance rotational stability of the humeral stem 402, initially due to their distal edges digging into adjacent bone and long-term due to bone growth proximally into the holes to the extent permitted by the articular component. Additionally, optionally, hole 430 may be included in an inserter interconnection or interface of the interior socket 422 for connection to an inserter instrument (not shown) for inserting and/or impacting the humeral stem 402 into a bone, such as a proximal humerus.

Figures 12A, 12B, 12C:
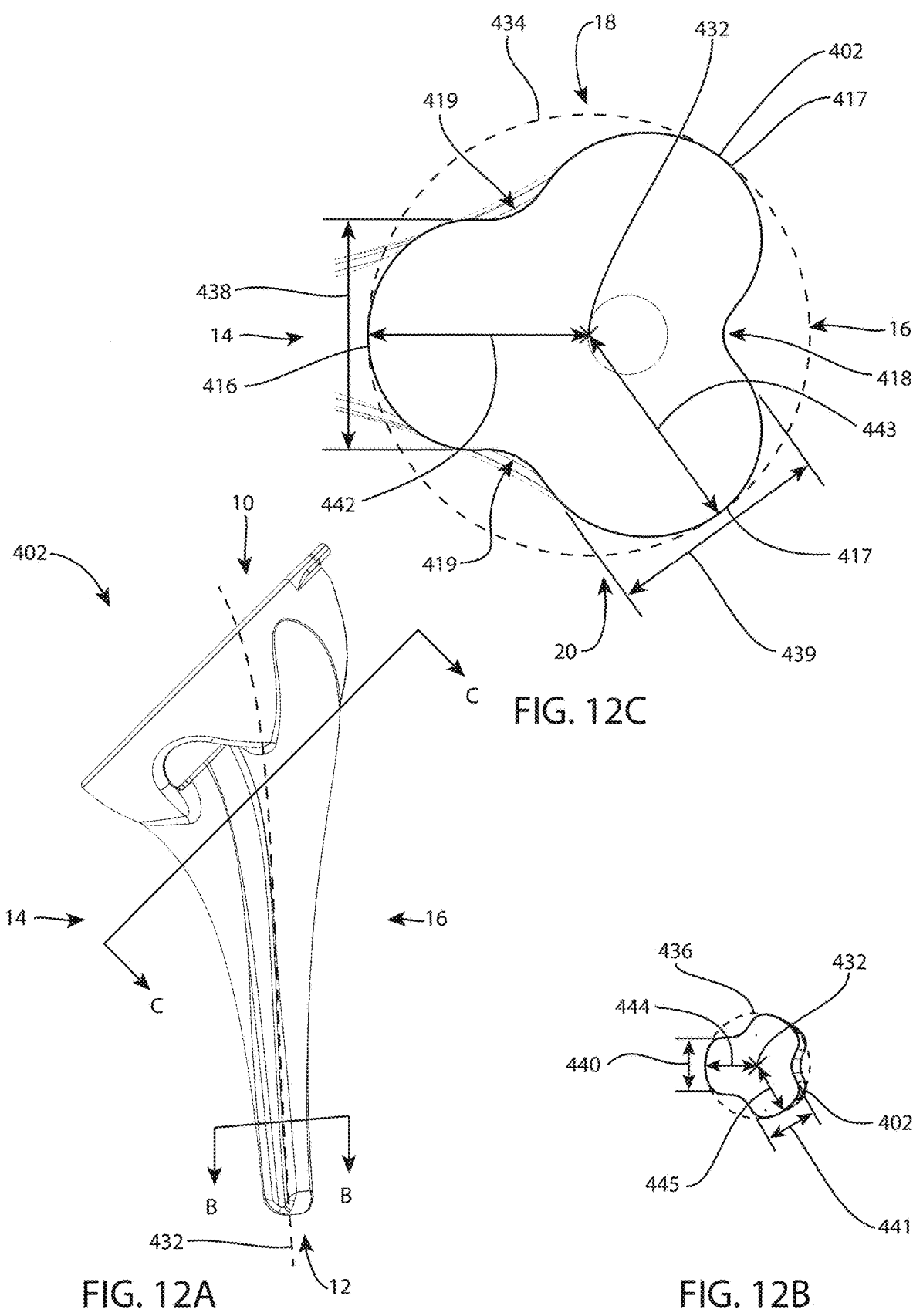
FIG. 12A is a posterior view of the humeral stem of FIG. 4.
FIG. 12B is a cross-sectional view of the humeral stem of FIG. 4, taken along section line B-B of FIG. 12A.
FIG. 12C is another cross-sectional view of the humeral stem of FIG. 4, taken along section line C-C of FIG. 12A.

The distal shaft 412 may extend distally from the exterior of the proximal body 410 to terminate at a free end 450 at the distal end 12. The distal shaft 412 may start out the same size or similar in size to the proximal body and may become smaller farther from the proximal body, towards the distal end 12. In other words, the distal shaft 412 may have a larger overall outer diameter at or near proximal body 410 and a smaller overall outer diameter farther from the proximal body, near the free end 450. FIG. 12C shows a proximal outer diameter 434 and FIG. 12B shows a distal outer diameter 436, which is smaller than outer diameter 434. The distal shaft 412 may include alternating longitudinal ridges and longitudinal grooves. The ridges may be described as arms, bars, beams, branches, columns, cylinders, fins, legs, limbs, lobes, pillars, rails, ribs, shafts, struts, or other geometrical shapes. This arrangement may enhance rotational stability along most or all of the length of the distal shaft 412 when the humeral stem 402 is implanted in a proximal humerus. The distal shaft 412 of humeral stem 402 has three ridges and three grooves, although any number of ridges and grooves may be present. The illustrated arrangement of three ridges and three grooves gives the distal shaft 412 a cross-sectional shape that may be described as tri-lobed, triangular, or Y-shaped (see FIGS. 12B-C). A medial ridge 416 and two oblique-lateral ridges 417 are shown; there is an antero-lateral ridge and a postero-lateral ridge. Each ridge 416, 417 has an arcuate or circular profile. A lateral groove 418 and two oblique-medial grooves 419 are shown; there is an antero-medial groove and a postero-medial groove. The ridges 416, 417 may merge together along some or all of the length of the distal shaft 412 to form a central longitudinal solid portion 420. The solid portion 420 may track along, or may define, a longitudinal centerline 432. The centerline 432 may be straight or linear, or it may be curved, bent, irregular, and so on. Referring to FIG. 12A, at least the distal portion of the centerline 432 may be straight or linear in a posterior (or anterior) view. Referring to FIGS. 8A and 8C, the entire centerline 432 may be straight or linear in medial or lateral views.

Referring to FIGS. 12B-C, each ridge 416, 417 may extend transversely away from the centerline 432 a first distance near the proximal body 410 and a second distance farther from the proximal body (closer to the free end). For each ridge 416, 417 the second distance may be less than the first distance. The ridges 416, 417 and/or grooves 418, 419 may be wider near the proximal end 10 of the distal shaft 412 and narrower near the distal end 12. FIG. 12C shows a proximal distance 442 and a proximal transverse width 438 of ridge 416 and a proximal distance 443 and a proximal transverse width 439 of postero-lateral ridge 417. FIG. 12B shows a distal distance 444 and a distal transverse width 440 of ridge 416 and a distal distance 445 and a distal transverse width 441 of postero-lateral ridge 417. Distal distance 444 is smaller than proximal distance 442, distal distance 445 is smaller than proximal distance 443, distal width 440 is less than proximal width 438, and distal width 441 is less than proximal width 439. Furthermore, even if section lines B-B and C-C were each drawn at some other transverse angle relative to the centerline 432 at their respective proximal-distal locations, the distal outer diameter, distances 444, 445, and widths 440, 441 would still be less than the proximal outer diameter, distances 442, 443, and widths 438, 439 respectively.

The proximal and distal distances 442, 443 and 444, 445 and/or the proximal and distal transverse widths 438, 439 and 440, 441 for each ridge 416, 417 may be the same as, or different from, the corresponding proximal and distal distances of the other ridges of the distal shaft 412. In the example shown, with three ridges 416, 417, there may be three unique proximal distances, three unique distal distances, three unique proximal transverse widths, and/or three unique distal transverse widths. In the example shown, the antero-lateral and postero-lateral ridges 417 are identical mirror images of each other, while the medial ridge 416 is different from the ridges 417. The differences are more pronounced near the proximal body 410. Optionally, the distal distances 444, 445 may be equal and/or the distal widths 440, 441 may be equal.

Figures 5A, 5B:
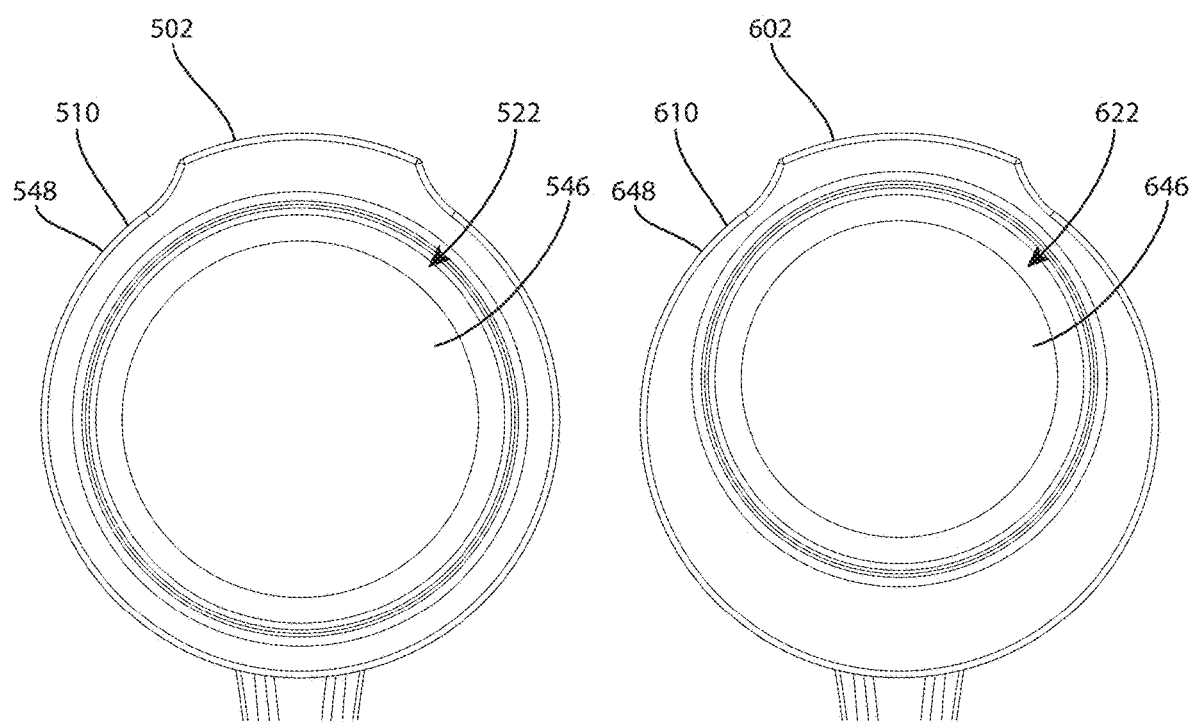
FIG. 5A is a view perpendicular to a bottom surface of a socket of yet another humeral stem.
FIG. 5B is a view perpendicular to a bottom surface of a socket of yet another humeral stem.

Referring to FIG. 5A, a humeral stem 502 is shown with an interior socket 522 with features shaped to receive an articular component, such as concave articular component 104 or convex articular component 204. The interior socket 522 may include a flat bottom surface 546 which may be parallel to a proximal rim 548 of the proximal body 510. The interior socket 522 may connect to an articular component so that the articular component is concentric within the proximal body 510.

Referring to FIG. 5B, a humeral stem 602 is shown with an interior socket 622 with features shaped to receive an articular component, such as concave articular component 104 or convex articular component 204. The interior socket 622 may include a flat bottom surface 646 which may be parallel to a proximal rim 648 of the proximal body 610. The interior socket 622 may connect to an articular component so that the articular component is eccentric within the proximal body 610. The interior socket 622 may be offset anteriorly, posteriorly, medially, laterally as shown, or obliquely.

Figure 6A:
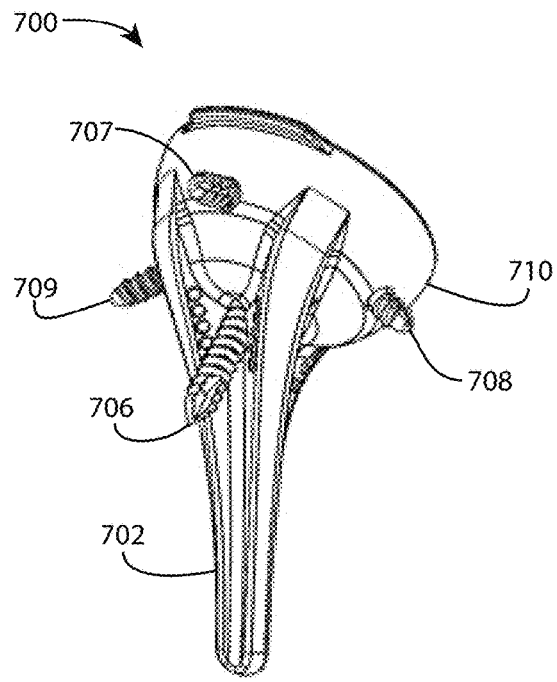
FIG. 6A is an oblique view of another humeral implant with a humeral stem and fasteners.
Figure 6B:
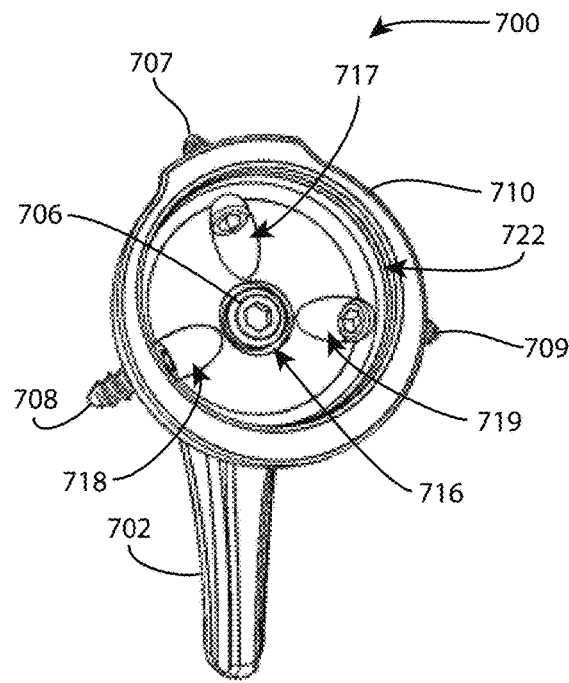
FIG. 6B is another oblique view of the humeral implant of FIG. 6A from a different direction.

Referring to FIGS. 6A-B, a humeral implant 700 includes a humeral stem 702 and may include one or more fasteners, such as the four screws 706, 707, 708, 709 shown. An articular component such as concave articular component 104 or convex articular component 204 may also be included. Humeral stem 702 includes a proximal body 710 having an interior socket 722. One or more fastener holes may extend from the interior socket 722 outwardly through the proximal body 710. Four holes 716, 717, 718, 719 are shown. Hole 716 is centered in the interior socket 722, extends infero-laterally, and receives screw 706. Hole 717 is superior to hole 716, extends supero-laterally, and receives screw 707. Hole 718 is inferior and anterior to hole 716, extends inferiorly, anteriorly, and laterally, and receives screw 708. Hole 719 is inferior and posterior to hole 716, extends inferiorly, posteriorly, and laterally, and receives screw 709.

Figure 7A:
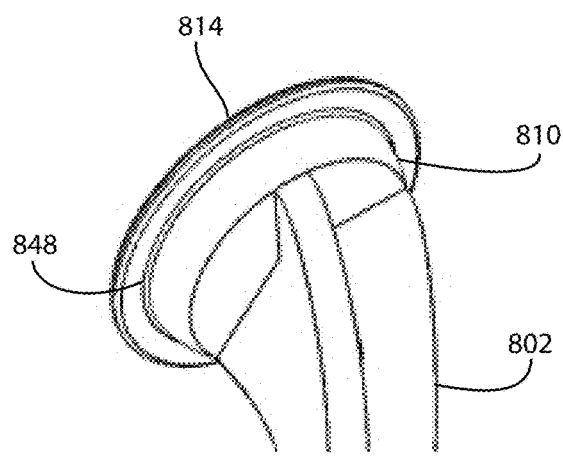
FIG. 7A is an oblique detail view of a portion of yet another humeral stem.

Referring to FIG. 7A, a humeral stem 802 includes a proximal body 810 with a proximal rim 848. A circumferential flange 814 may extend around the entire rim 848.

Figure 7B:
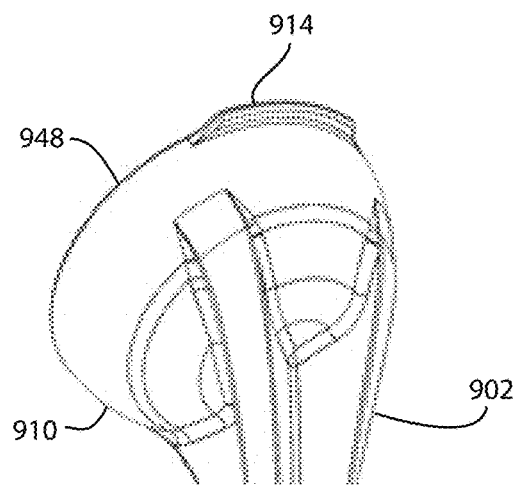
FIG. 7B is an oblique detail view of a portion of yet another humeral stem.

Referring to FIG. 7B, a humeral stem 902 includes a proximal body 910 with a proximal rim 948. A partial flange 914 extends outwardly from a lateral portion of the rim 948.

Referring to FIGS. 10A-11B, a humeral stem 1002 includes a proximal body 1010 and a distal shaft 1012. In an embodiment, the distal shaft 1012 may be integrally formed with the proximal body 1010 to form a one-piece humeral stem 1002.

The proximal body 1010 may have a generally hemispherical exterior shape and an interior socket 1022 with features shaped to receive an articular component, such as concave articular component 104 or convex articular component 204. The interior socket 1022 may include a flat bottom surface 1046 which may be parallel to a proximal rim 1048 of the proximal body 1010. The exterior of proximal body 1010 may match one of the proximal bodies 310, 320, 330 of FIGS. 3A-C. The interior socket 1022 may be referred to as an articular component interconnection or interface. A partial or continuous flange 1014 may extend medially, anteriorly, laterally, and/or posteriorly from the proximal end 10 of the proximal body 1010. A lateral partial flange 1014 is shown extending from the rim 1048. One or more holes may extend through the proximal body 1010; a hole 1030 is shown. Hole 1030 is shown with a circular cross-sectional shape, which may be internally threaded. The hole 1030 may be included in an inserter interconnection or interface of the interior socket 1022 for connection to an inserter instrument (not shown) for inserting and/or impacting the humeral stem 1002 into a bone, such as a proximal humerus. After the humeral stem 1002 is fully seated and the inserter is disconnected from hole 1030, a fastener may be inserted in hole 1030.

The distal shaft 1012 may extend distally from the exterior of the proximal body 1010 to terminate at a free end 1050 at the distal end 12. The distal shaft 1012 may start out the same size or similar in size to the proximal body and may become smaller farther from the proximal body, towards the distal end 12. In other words, like stem 402, the distal shaft 1012 may have a larger overall outer diameter at or near proximal body 1010 and a smaller overall outer diameter farther from the proximal body, near the free end 1050. The distal shaft 1012 may include alternating longitudinal ridges and longitudinal grooves. The ridges may be described as arms, bars, beams, branches, columns, cylinders, fins, legs, limbs, lobes, pillars, rails, ribs, shafts, struts, or other geometrical shapes. This arrangement may enhance rotational stability along most or all of the length of the distal shaft 1012 when the humeral stem 1002 is implanted in a proximal humerus. The distal shaft 1012 of humeral stem 1002 has three ridges and three grooves, although any number of ridges and grooves may be present. The illustrated arrangement of three ridges and three grooves gives the distal shaft 1012 a cross-sectional shape that may be described as tri-lobed, triangular, or Y-shaped. A medial ridge 1016 and two oblique-lateral ridges 1017 are shown; there is an antero-lateral ridge and a postero-lateral ridge. Each ridge 1016, 1017 has a rectangular cross-sectional profile which may have its longest dimension oriented radially outwardly relative to the centerline 1032. A lateral groove 1018 and two oblique-medial grooves 1019 are shown; there is an antero-medial groove and a postero-medial groove. The ridges 1016, 1017 may merge together along some or all of the length of the distal shaft 1012 to form a central longitudinal solid portion 1020. The solid portion 1020 may track along, or may define, a longitudinal centerline 1032. The centerline 1032 may be straight or linear, or it may be curved, bent, irregular, and so on. Referring to FIG. 10B, at least the distal portion of the centerline 1032 may be straight or linear in a posterior (or anterior) view. Referring to FIGS. 10A and 10C, the entire centerline 1032 may be straight or linear in medial or lateral views.

Each ridge 1016, 1017 may extend transversely away from the centerline 1032 a first distance near the proximal body 1010 and a second distance farther from the proximal body (closer to the free end). Like stem 402, for each ridge 1016, 1017 the second distance may be less than the first distance. The ridges 1016, 1017 and/or grooves 1018, 1019 may be wider near the proximal end 10 of the distal shaft 1012 and narrower near the distal end 12.

Like stem 402, the proximal and distal distances and/or the proximal and distal transverse widths for each ridge 1016, 1017 may be the same as, or different from, the corresponding proximal and distal distances of the other ridges of the distal shaft 1012.

Referring to FIG. 14, a humeral stem 1102 includes a proximal body 1110 and a distal shaft 1112 with longitudinal ridges 1116, 1117. Multiple holes 1120 may extend through the proximal body 1110 and/or ridges 1116, 1117 and/or elsewhere on the humeral stem 1102. Sutures, cables, or other lines may be routed through the holes 1120 to re-attach soft tissues or bone fragments to the humerus.

Referring to FIG. 15A-D, a humeral stem 1202 includes a proximal body 1210 and a distal shaft 1212. In an embodiment, the distal shaft 1212 may be integrally formed with the proximal body 1210 to form a one-piece humeral stem 1202.

The proximal body 1210 may have a generally hemispherical exterior shape and an interior socket (not visible). The exterior of proximal body 1210 may match one of the proximal bodies 310, 320, 330 of FIGS. 3A-C. A partial or continuous flange 1214 may extend medially, anteriorly, laterally, and/or posteriorly from the proximal end 10 of the proximal body 1210. A continuous circumferential flange 1214 is shown. A hole 1230 may extend infero-laterally through the center bottom of the interior socket for connection to an inserter or to receive a fastener. A boss 1226 may extend distally around the hole 1230.

The distal shaft 1212 may include alternating longitudinal ridges 1216 and grooves 1218 similar to those described for preceding embodiments. Three ridges 1216 and three grooves 1218 are shown. The illustrated arrangement of three ridges and three grooves gives the distal shaft 1212 a cross-sectional shape that may be described as tri-lobed, triangular, or Y-shaped. The ridges 1216 in this example are merged together distally to form a central longitudinal solid portion 1220, and they separate from each other near the proximal body 1210 into three separate columns surrounding a cavity 1224. The hole 1230 and the cavity 1224 may be open to each other. A pattern of smaller longitudinal ridges 1232 and grooves 1234 is superimposed along each main ridge 1216.

Figure 16A:
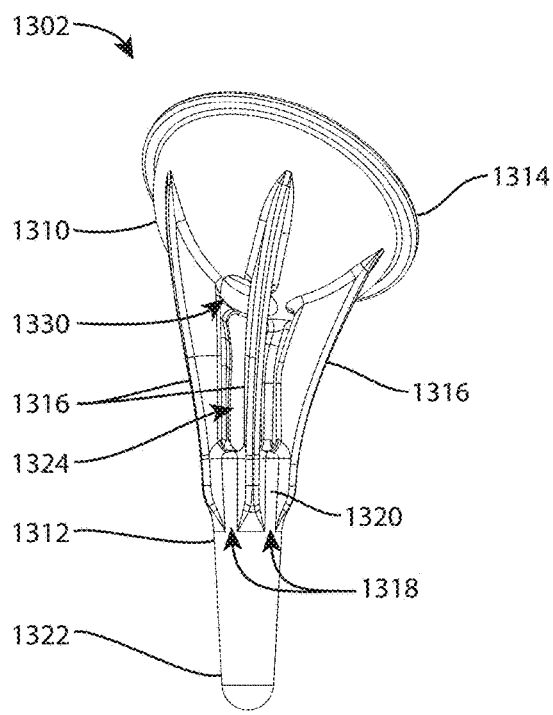
FIG. 16A is an oblique view of yet another humeral stem.

Referring to FIG. 16A, a humeral stem 1302 includes a proximal body 1310 and a distal shaft 1312. In an embodiment, the distal shaft 1312 may be integrally formed with the proximal body 1310 to form a one-piece humeral stem 1302.

The proximal body 1310 may have a generally hemispherical exterior shape and an interior socket (not visible). The exterior of proximal body 1310 may match one of the proximal bodies 310, 320, 330 of FIGS. 3A-C. A partial or continuous flange 1314 may extend medially, anteriorly, laterally, and/or posteriorly from the proximal end 10 of the proximal body 1310. A continuous circumferential flange 1314 is shown. A hole 1330 may extend infero-laterally through the center bottom of the interior socket for connection to an inserter or to receive a fastener.

The distal shaft 1312 may include alternating longitudinal ridges 1316 and grooves 1318 similar to those described for preceding embodiments. Five ridges 1316 and five grooves 1318 are shown, which extend distally along only a portion of the distal shaft 1312. The illustrated arrangement of five ridges and five grooves gives the distal shaft 1312 a cross-sectional shape that may be described as penta-lobed or star-shaped. The ridges 1316 in this example are merged together distally to form a central longitudinal solid portion 1320, and they separate from each other near the middle of the proximal-distal length of the humeral stem 1302 into five separate columns surrounding a cavity 1324. The hole 1330 and the cavity 1324 may be open to each other. The ridges 1316 in this example have rectangular cross-sectional profiles with transverse widths much smaller than the preceding embodiments. Like humeral stem 1002, the ridges 1316 may have their longest dimensions oriented radially outwardly relative to the centerline of the humeral stem 1302. The ridges 1316 are raised relative to the solid portion 1320. A smooth section 1322 of the solid portion 1320 extends distally past the distal ends of the ridges 1316.

Figure 16B:
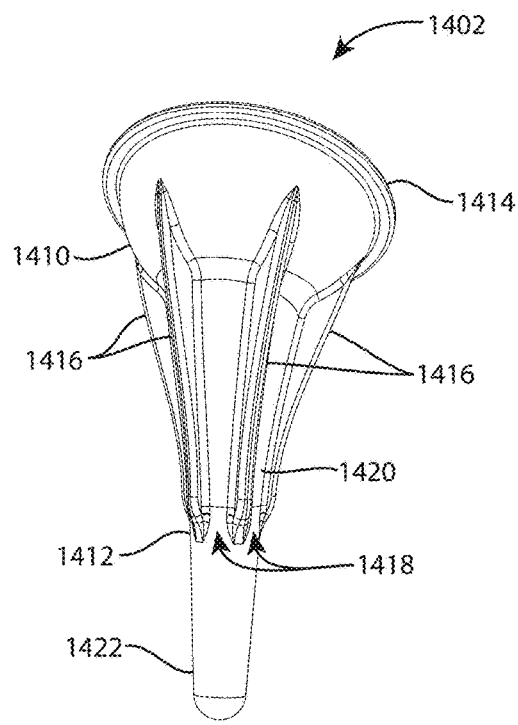
FIG. 16B is an oblique view of yet another humeral stem.

Referring to FIG. 16B, a humeral stem 1402 includes a proximal body 1410 and a distal shaft 1412. In an embodiment, the distal shaft 1412 may be integrally formed with the proximal body 1410 to form a one-piece humeral stem 1402.

The proximal body 1410 may have a generally hemispherical exterior shape and an interior socket (not visible). The exterior of proximal body 1410 may match one of the proximal bodies 310, 320, 330 of FIGS. 3A-C. A partial or continuous flange 1414 may extend medially, anteriorly, laterally, and/or posteriorly from the proximal end 10 of the proximal body 1410. A continuous circumferential flange 1414 is shown.

The distal shaft 1412 may include alternating longitudinal ridges 1416 and grooves 1418 similar to those described for preceding embodiments. Five ridges 1416 and five grooves 1418 are included in this design, which extend distally along only a portion of the distal shaft 1412. The illustrated arrangement of five ridges and five grooves gives the distal shaft 1412 a cross-sectional shape that may be described as penta-lobed or star-shaped. The ridges 1416 in this example are merged together to form a central longitudinal solid portion 1420, which extends the full length of the distal shaft 1412. The ridges 1416 in this example have rectangular profiles with narrow transverse widths similar to humeral stem 1302. The ridges 1416 are raised relative to the solid portion 1420. A smooth section 1422 of the solid portion 1420 extends distally past the distal ends of the ridges 1416.

A variation of humeral stem 1402 (not shown) may lack the longitudinal ridges 1416 and grooves 1418 altogether, so that the distal shaft 1412 comprises the central longitudinal solid portion 1420 alone.

Figure 17:
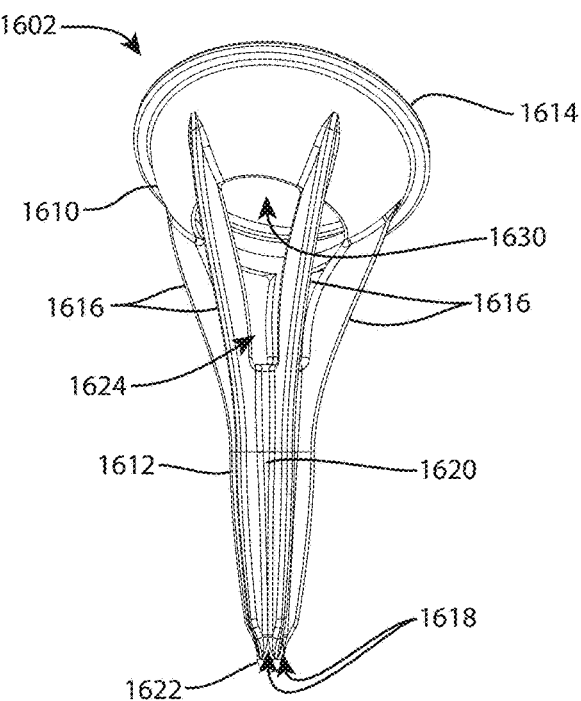
FIG. 17 is an oblique view of yet another humeral stem.

Referring to FIG. 17, a humeral stem 1602 includes a proximal body 1610 and a distal shaft 1612. In an embodiment, the distal shaft 1612 may be integrally formed with the proximal body 1610 to form a one-piece humeral stem 1602.

The proximal body 1610 may have a generally hemispherical exterior shape and an interior socket (not visible). The exterior of proximal body 1610 may match one of the proximal bodies 310, 320, 330 of FIGS. 3A-C. A partial or continuous flange 1614 may extend medially, anteriorly, laterally, and/or posteriorly from the proximal end 10 of the proximal body 1610. A continuous circumferential flange 1614 is shown. A hole 1630 may extend infero-laterally through the center bottom of the interior socket for connection to an inserter or to receive a fastener.

The distal shaft 1612 may include alternating longitudinal ridges 1616 and grooves 1618 similar to those described for preceding embodiments. Five ridges 1616 and five grooves 1618 are shown, which extend distally along nearly the entire distal shaft 1612. Thus, the distal shaft 1612 may have a cross-sectional shape that may be described as penta-lobed or star-shaped. The ridges 1616 in this example are merged together distally to form a central longitudinal solid portion 1620, and they separate from each other near the middle of the proximal-distal length of the humeral stem 1602 into five separate columns surrounding a cavity 1624. The hole 1630 and the cavity 1624 are open to each other. The ridges 1616 in this example have rectangular profiles with transverse widths much smaller than the preceding embodiments, similar to humeral stems 1302, 1402. The ridges 1616 are raised relative to the solid portion 1620. A short smooth distal tip portion 1622 extends distally past the distal ends of the ridges 1616.

A first variation of the humeral stem 1602 may lack the hole 1630 and/or the cavity 1624 so that the distal shaft 1612 is solid. A second variation of the humeral stem 1602 may lack the hole 1630, cavity 1624, ridges 1616, and grooves 1618 so that the distal shaft 1612 comprises the central longitudinal solid portion 1620 alone.

Figure 18:
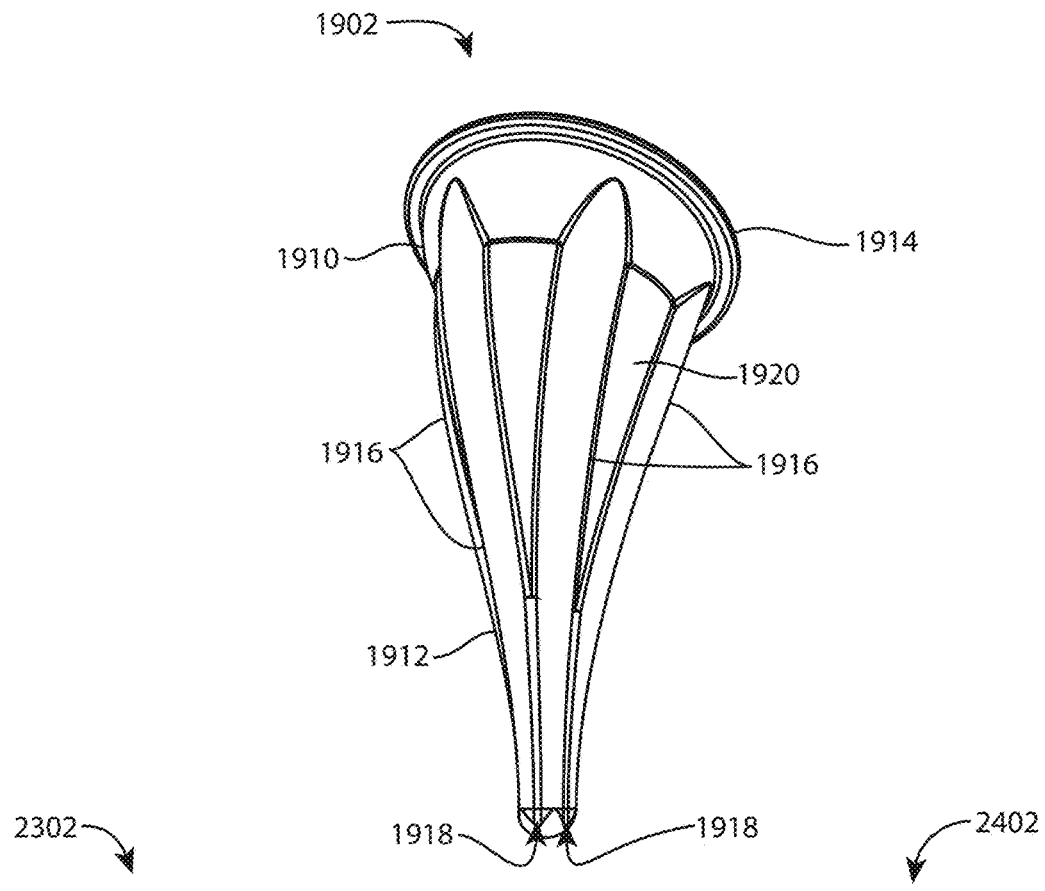
FIG. 18 is an oblique view of yet another humeral stem.

Referring to FIG. 18, a humeral stem 1902 includes a proximal body 1910 and a distal shaft 1912. In an embodiment, the distal shaft 1912 may be integrally formed with the proximal body 1910 to form a one-piece humeral stem 1902.

The proximal body 1910 may have a generally hemispherical exterior shape and an interior socket (not visible). The exterior of proximal body 1910 may match one of the proximal bodies 310, 320, 330 of FIGS. 3A-C. A partial or continuous flange 1914 may extend medially, anteriorly, laterally, and/or posteriorly from the proximal end 10 of the proximal body 1910. A continuous circumferential flange 1914 is shown.

The distal shaft 1912 may include alternating longitudinal ridges 1916 and grooves 1918 similar to those described for preceding embodiments. Five ridges 1916 and five grooves 1918 are shown, which extend distally along the distal shaft 1912 to give it a cross-sectional shape that may be described as penta-lobed or star-shaped. The ridges 1916 in this example are merged together with a central longitudinal solid portion 1920. The ridges 1916 in this example have arcuate or circular profiles similar to humeral stem 402.

A first variation of the humeral stem 1902 may have a solid portion 1920 with a smaller outer diameter than that shown, so that the ridges 1916 and grooves 1918 are much more prominent. A second variation of the humeral stem 1902 may lack the solid portion 1920 so that the ridges 1916 are separate columns, optionally merged together very close to the distal end.

Figure 19A:
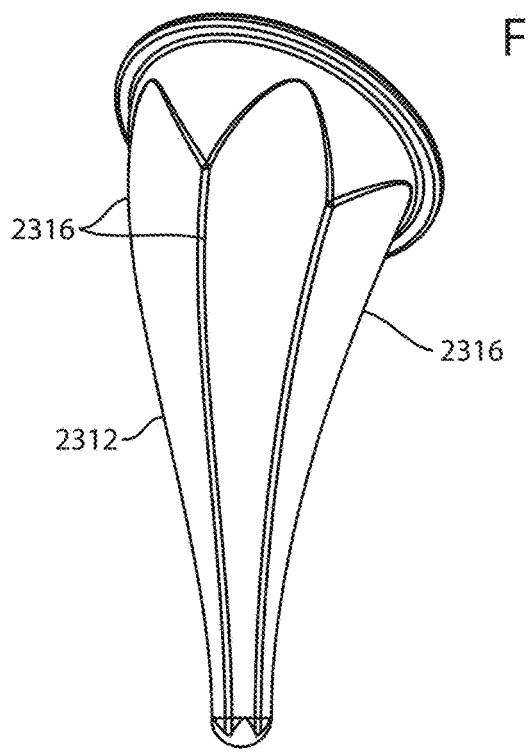
FIG. 19A is an oblique view of yet another humeral stem.

Referring to FIG. 19A, a humeral stem 2302 may be thought of as another variant of humeral stem 1902, in which the cross-sectional diameters of each ridge 2316 are large enough relative to the cross-sectional diameter of the distal shaft 2312 that a central longitudinal solid portion, if present, is not visible because the ridges 2316 merge directly with each other.

Figure 19B:
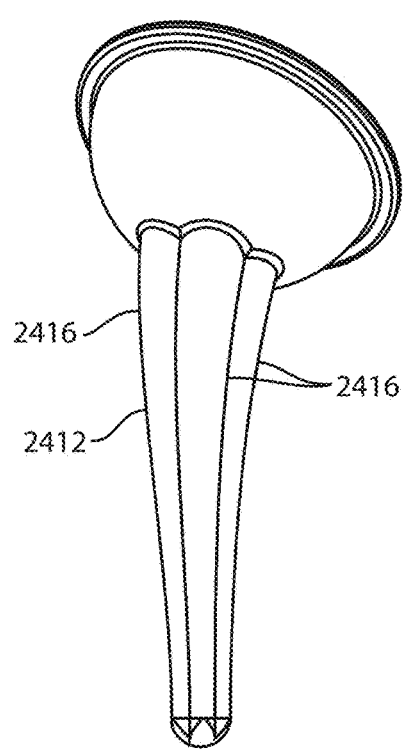
FIG. 19B is an oblique view of yet another humeral stem.

Referring to FIG. 19B, a humeral stem 2402 may be thought of as a variation of humeral stem 2302, in which the cross-sectional diameters of the distal shaft 2412 and ridges 2416 are smaller, but still proportioned so that a central longitudinal solid portion, if present, is not visible because the ridges 2416 merge directly with each other.

Figure 20A:
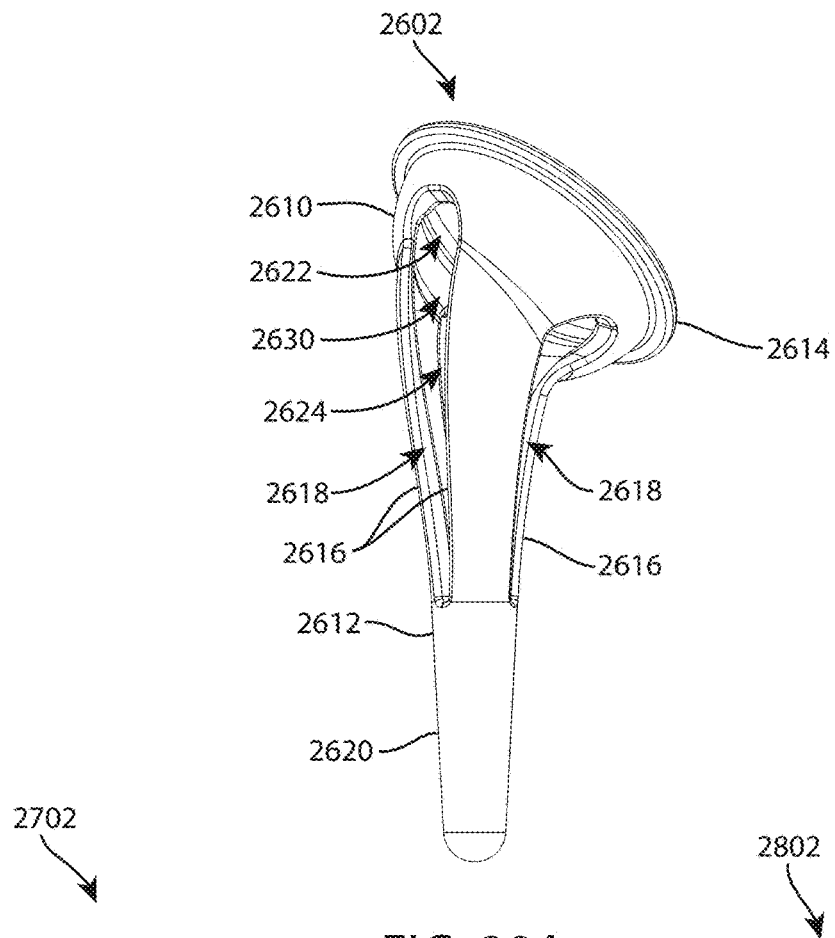
FIG. 20A is an oblique view of yet another humeral stem.

Referring to FIG. 20A, a humeral stem 2602 includes a proximal body 2610 and a distal shaft 2612. In an embodiment, the distal shaft 2612 may be integrally formed with the proximal body 2610 to form a one-piece humeral stem 2602.

The proximal body 2610 may have a generally hemispherical exterior shape and an interior socket 2622. The exterior of proximal body 2610 may match one of the proximal bodies 310, 320, 330 of FIGS. 3A-C. A partial or continuous flange 2614 may extend medially, anteriorly, laterally, and/or posteriorly from the proximal end 10 of the proximal body 2610. A continuous circumferential flange 2614 is shown. A hole 2630 may extend through the center bottom of the interior socket.

The distal shaft 2612 may include alternating longitudinal columns 2616 and windows 2618. Three columns 2616 and three windows 2618 are shown, which extend distally along a proximal portion of the distal shaft 1412. The columns 2616 in this example merge together distally to form a central longitudinal solid portion 2620, and they separate from each other near the middle of the proximal-distal length of the humeral stem 2602 into three separate columns surrounding a cavity 2624. Thus, the distal shaft 2612 has a cross-sectional shape that may be described as tri-lobed, triangular, or Y-shaped. The hole 2630, the windows 2618, and the cavity 2624 are open to each other. The columns 2616 in this example have rectangular cross-sectional profiles which may have their shortest dimension oriented radially outwardly relative to the centerline and their longest dimension oriented circumferentially relative to the outer diameter of the distal shaft 2612. The columns 2616 in this example are even or flush relative to the solid portion 2620. The cavity 2624 may receive bone graft intraoperatively, or other means for promoting bony integration may be included internally.

Figure 20B:
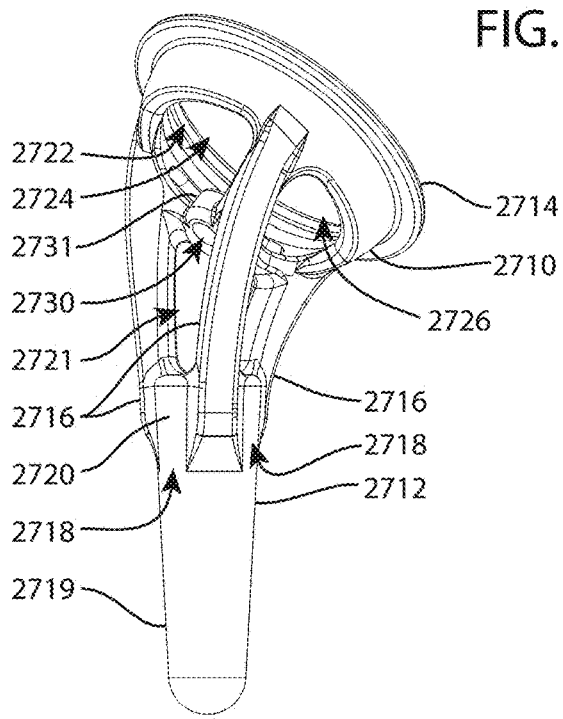
FIG. 20B is an oblique view of yet another humeral stem.

Referring to FIG. 20B, a humeral stem 2702 includes a proximal body 2710 and a distal shaft 2712. In an embodiment, the distal shaft 2712 may be integrally formed with the proximal body 2710 to form a one-piece humeral stem 2702.

The proximal body 2710 may have a generally hemispherical exterior shape and an interior socket 2722. The exterior of proximal body 2710 may match one of the proximal bodies 310, 320, 330 of FIGS. 3A-C. A partial or continuous flange 2714 may extend medially, anteriorly, laterally, and/or posteriorly from the proximal end 10 of the proximal body 2710. A continuous circumferential flange 2714 is shown. One or more holes may extend through the proximal body 410. Two holes 2724, 2726 are shown and a third hole is not easily visible, but is a mirror image of hole 2726. The holes 2724, 2726 have non-circular cross-sectional shapes which may be based upon the geometry of the corresponding ridges 2716 and grooves 2718 in the vicinity of the holes. Hole 2730 extends infero-laterally through the center bottom of the interior socket 2722 and has a circular cross-sectional shape which may be surrounded by a boss 2731. The holes 2724, 2726, and/or 2730 may provide means or openings for inserting instruments to aid in removing or extracting the implant from the bone after implantation. The non-circular holes may enhance rotational stability of the humeral stem 2702, initially due to their distal edges digging into adjacent bone and long-term due to bone growth proximally into the holes to the extent permitted by the articular component. Additionally, optionally, hole 2730 may be included in an inserter interconnection or interface of the interior socket 2722 for connection to an inserter instrument (not shown) for inserting and/or impacting the humeral stem 2702 into a bone, such as a proximal humerus.

The distal shaft 2712 may include alternating longitudinal ridges 2716 and grooves 2718 similar to those described for preceding embodiments. Three ridges 2716 and three grooves 2718 are shown, which extend distally along only a portion of the distal shaft 2712. The illustrated arrangement of three ridges and three grooves gives the distal shaft 2712 a cross-sectional shape that may be described as tri-lobed, triangular, or Y-shaped. The ridges 2716 in this example are merged together distally to form a central longitudinal solid portion 2720, and they separate from each other near the middle of the proximal-distal length of the humeral stem 2702 into three separate columns surrounding a cavity 2721. The non-circular holes, hole 2730, and the cavity 2721 may be open to each other. The ridges 2716 in this example have rectangular cross-sectional profiles. Like humeral stem 1002, the ridges 2716 may have their longest dimensions oriented radially outwardly relative to the centerline of the humeral stem 2702. The ridges 2716 are raised relative to the solid portion 2720. A smooth section 2719 of the solid portion 2720 extends distally past the distal ends of the ridges 2716.

Figure 20C:
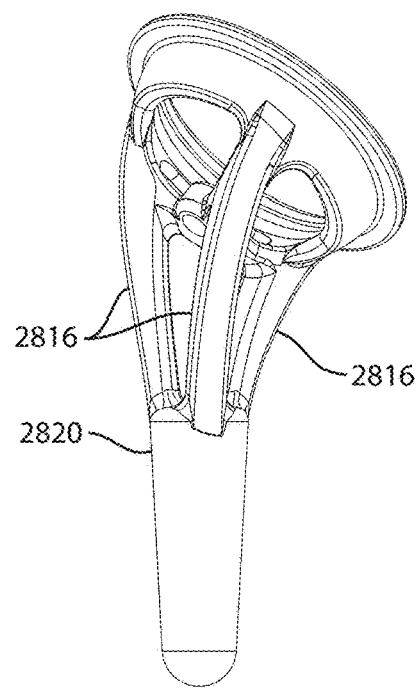
FIG. 20C is an oblique view of yet another humeral stem.

Referring to FIG. 20C, a humeral stem 2802 may be thought of as a variant of humeral stem 2702, in which the ridges 2816 are even or flush relative to the central longitudinal solid portion 2820.

Figure 21A:
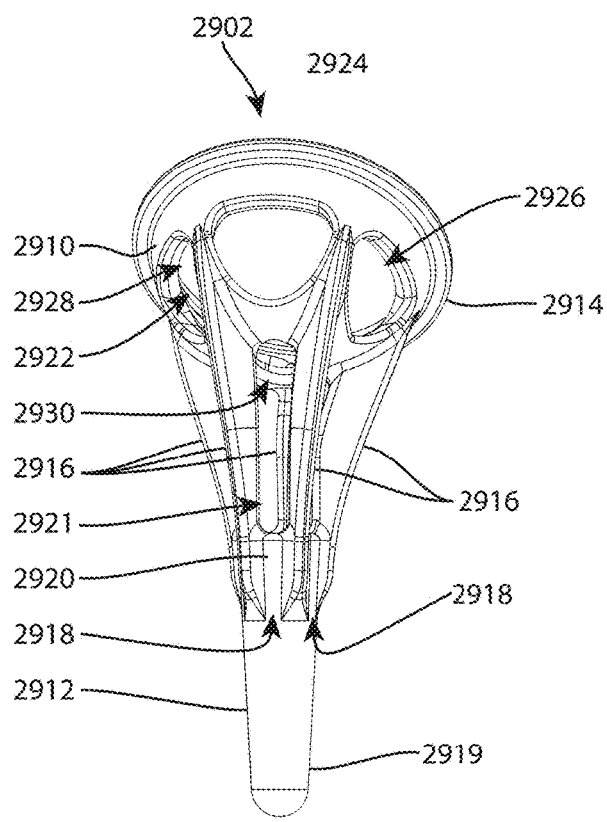
FIG. 21A is an oblique view of yet another humeral stem.

Referring to FIG. 21A, a humeral stem 2902 includes a proximal body 2910 and a distal shaft 2912. In an embodiment, the distal shaft 2912 may be integrally formed with the proximal body 2910 to form a one-piece humeral stem 2902.

The proximal body 2910 may have a generally hemispherical exterior shape and an interior socket 2922. The exterior of proximal body 2910 may match one of the proximal bodies 310, 320, 330 of FIGS. 3A-C. A partial or continuous flange 2914 may extend medially, anteriorly, laterally, and/or posteriorly from the proximal end 10 of the proximal body 2910. A continuous circumferential flange 2914 is shown. One or more holes may extend through the proximal body 410. This embodiment includes five noncircular holes arranged around a central circular hole through the bottom of the socket 2922. Three of the noncircular holes 2924, 2926, 2928 are shown; fourth and fifth noncircular holes are not easily visible. The holes 2924, 2926, 2928 have non-circular cross-sectional shapes which may be based upon the geometry of the corresponding ridges 2916 and grooves 2918 in the vicinity of the holes. Hole 2930 extends distally through the center bottom of the interior socket 2922 and has a circular cross-sectional shape. The holes 2924, 2926, 2928, and/or 2930 may provide means or openings for inserting instruments to aid in removing or extracting the implant from the bone after implantation. The five noncircular holes may enhance rotational stability of the humeral stem 2902, initially due to their distal edges digging into adjacent bone and long-term due to bone growth proximally into the holes to the extent permitted by the articular component. Additionally, optionally, hole 2930 may be included in an inserter interconnection or interface of the interior socket 2922 for connection to an inserter instrument (not shown) for inserting and/or impacting the humeral stem 2902 into a bone, such as a proximal humerus.

The distal shaft 2912 may include alternating longitudinal ridges 2916 and grooves 2918 similar to those described for preceding embodiments. Five ridges 2916 and five grooves 2918 are shown, which extend distally along only a portion of the distal shaft 2912. The illustrated arrangement of five ridges and five grooves gives the distal shaft 2912 a cross-sectional shape that may be described as penta-lobed or star-shaped. The ridges 2916 in this example are merged together distally to form a central longitudinal solid portion 2920, and they separate from each other near the middle of the proximal-distal length of the humeral stem 2902 into three separate columns surrounding a cavity 2921. One or more of the six holes described for the proximal body 2910 may be open to the cavity 2921. The ridges 2916 in this example have rectangular cross-sectional profiles with narrow transverse widths similar to humeral stem 1302. Like humeral stem 1002, the ridges 2916 may have their longest dimensions oriented radially outwardly relative to the centerline of the humeral stem 2902. The ridges 2916 are raised relative to the solid portion 2920. A smooth section 2919 of the solid portion 2920 extends distally past the distal ends of the ridges 2916.

Figure 21B:
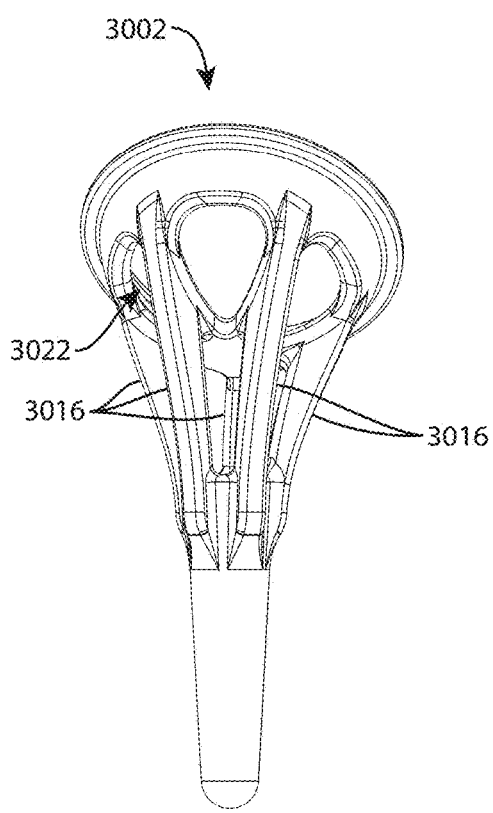
FIG. 21B is an oblique view of yet another humeral stem.

Referring to FIG. 21B, a humeral stem 3002 may be thought of as a variant of humeral stem 2902, in which the transverse width of the ridges 3016 are wider, for example twice as wide as ridges 2916. This embodiment lacks a central hole through the bottom of the socket 3022.

Figure 22:
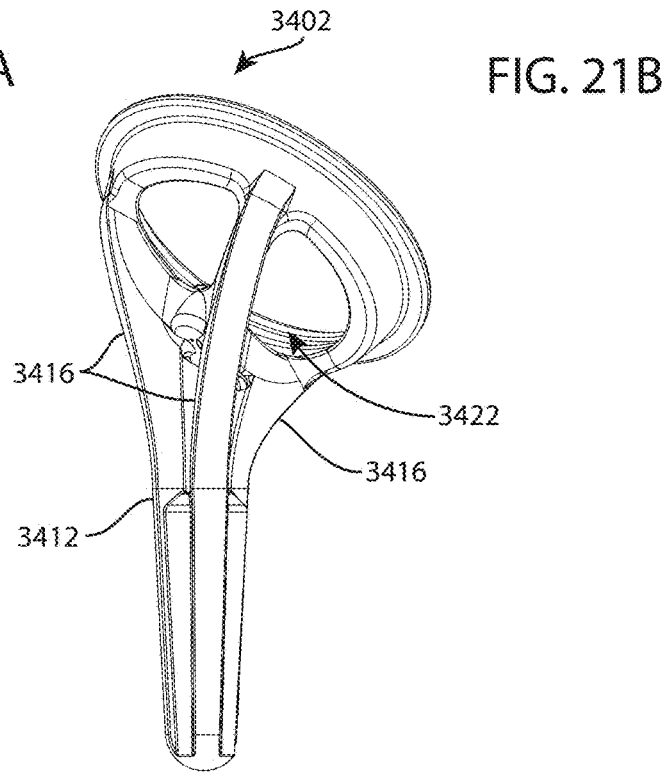
FIG. 22 is an oblique view of yet another humeral stem.

Referring to FIG. 22, a humeral stem 3402 may be thought of as a variant of humeral stem 2702, in which the ridges 3416 extend distally over the entire length of the distal shaft 3412. This embodiment lacks a central hole through the bottom of the socket 3422.

Figure 23:
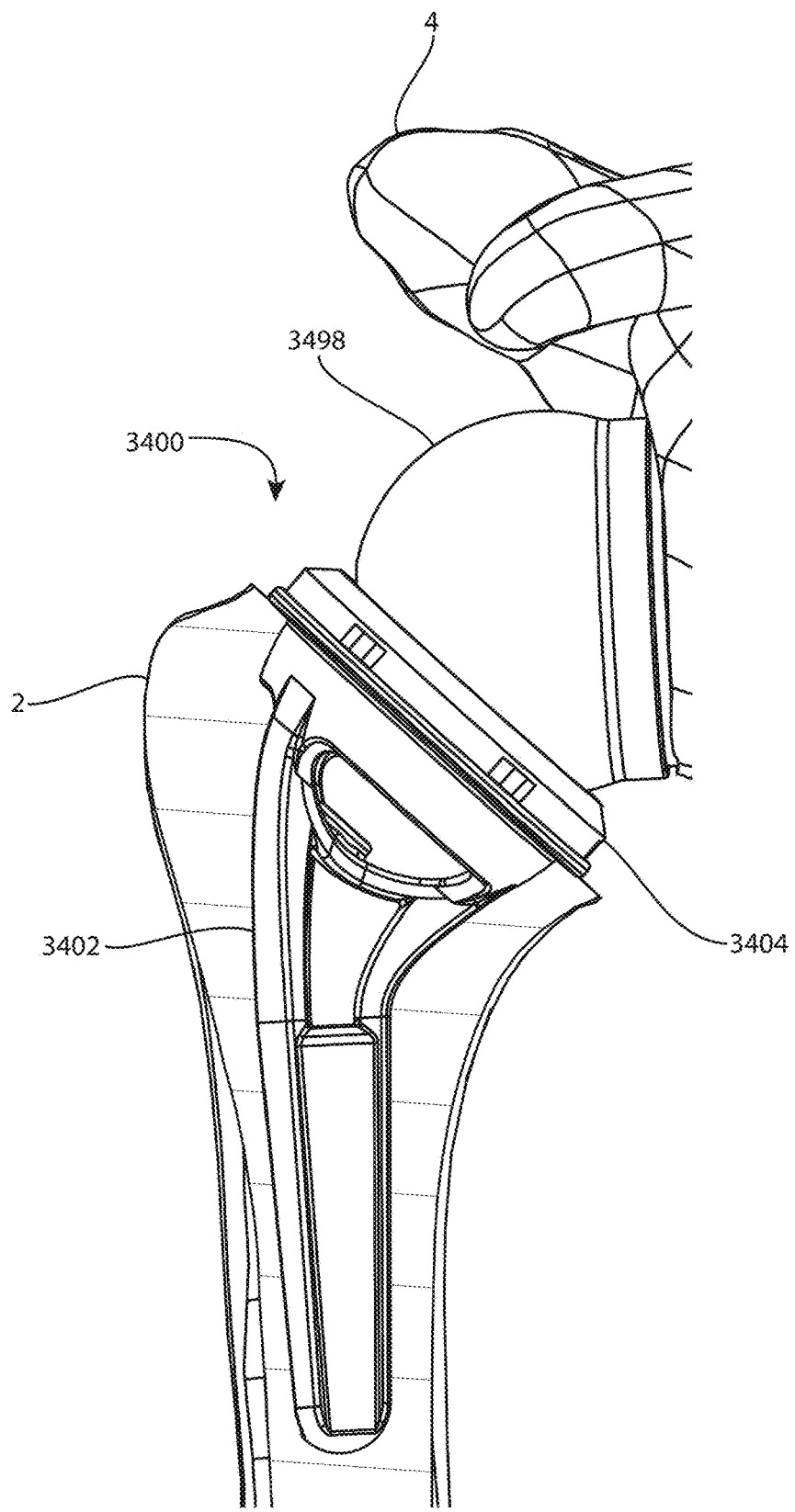
FIG. 23 is an anterior partial cross-sectional view of the humeral stem of FIG. 22 and a concave articular component implanted in a humerus, and a glenosphere implanted in a glenoid.
Figures 24A, 24B:
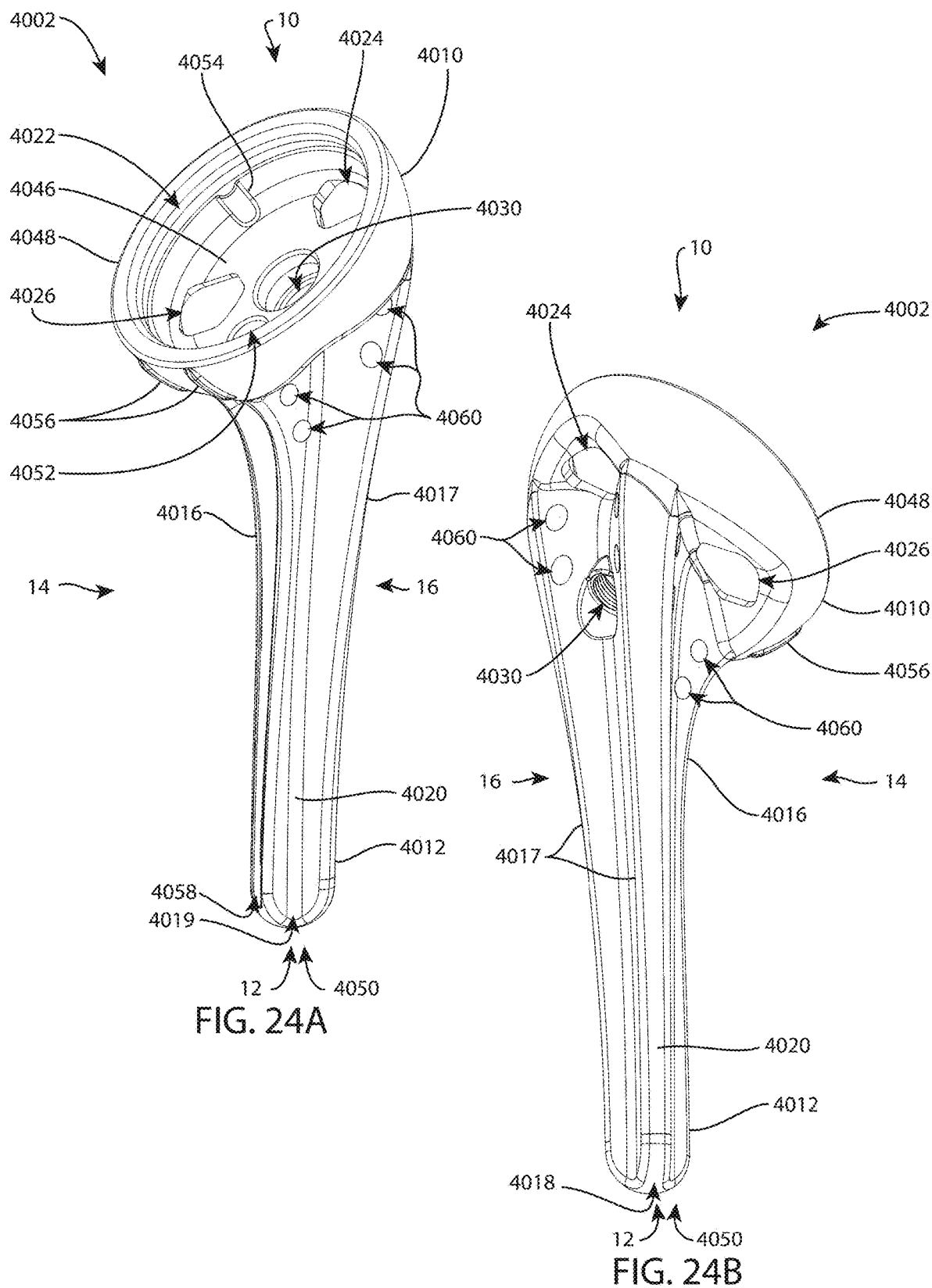
FIG. 24A is an oblique view of yet another humeral stem.
FIG. 24B is another oblique view of the humeral stem of FIG. 24A.

Referring to FIG. 23, a humeral implant 3400 includes the humeral stem 3402 and a humeral articular socket 3404. The humeral stem 3402 is shown implanted in a proximal humerus 2 and coupled to the humeral articular socket 3404. A glenosphere 3498 is shown implanted in a scapula 4 and articulating within the humeral articular socket 3404.

Referring to FIGS. 24A-F, a humeral stem 4002 includes a proximal body 4010 and a distal shaft 4012. In an embodiment, the distal shaft 4012 may be integrally formed with the proximal body 4010 to form a one-piece humeral stem 4002.

The proximal body 4010 may have a generally hemispherical exterior shape and an interior socket 4022 with features shaped to receive an articular component, such as concave articular component 104 or convex articular component 204. The exterior of proximal body 4010 may match one of the proximal bodies 310, 320, 330 of FIGS. 3A-C. A pair of external ridges 4056 may extend along the medial side 14 to enhance rotational stability. The interior socket 4022 may include a flat bottom surface 4046 which may be parallel to a proximal rim 4048 of the proximal body 4010. The interior socket 4022 may be referred to as an articular component interconnection or interface. This embodiment lacks a flange around the rim 4048. One or more holes may extend through the proximal body 4010; four holes 4024, 4026, 4028, 4030 are shown. Holes 4024, 4026, 4028 are shown with non-circular cross-sectional shapes which may be based upon the geometry of the corresponding ridges 4016, 4017 and grooves 4018, 4019 in the vicinity of the holes. Hole 4030 is shown with a circular cross-sectional shape, seen best in FIG. 24C, and may be internally threaded. The holes 4024, 4026, 4028, and/or 4030 may provide means or openings for inserting instruments to aid in removing or extracting the implant from the bone after implantation. Holes 4024, 4026, 4028 may enhance rotational stability of the humeral stem 4002, initially due to their distal edges digging into adjacent bone and long-term due to bone growth proximally into the holes to the extent permitted by the articular component. Additionally, optionally, hole 4030 may be included in an inserter interconnection or interface of the interior socket 4022 for connection to an inserter instrument (not shown) for inserting and/or impacting the humeral stem 4002 into a bone, such as a proximal humerus. A medial blind hole 4052 may extend into the bottom surface 4046 and partway through the proximal body 4010. A circular array of three ridges 4054 may be located around an inner wall of the interior socket 4022 and may extend perpendicular to the bottom surface 4046. Ridges 4054 may engage with corresponding grooves in the articular component to enhance rotational stability.

The distal shaft 4012 may extend distally from the exterior of the proximal body 4010 to terminate at a free end 4050 at the distal end 12. The distal shaft 4012 may start out the same size or similar in size to the proximal body and may become smaller farther from the proximal body, towards the distal end 12. In other words, the distal shaft 4012 may have a larger overall outer diameter at or near proximal body 4010 and a smaller overall outer diameter farther from the proximal body, near the free end 4050. The distal shaft 4012 may include alternating longitudinal ridges and longitudinal grooves. The ridges may be described as arms, bars, beams, branches, columns, cylinders, fins, legs, limbs, lobes, pillars, rails, ribs, shafts, struts, or other geometrical shapes. This arrangement may enhance rotational stability along most or all of the length of the distal shaft 4012 when the humeral stem 4002 is implanted in a proximal humerus. The distal shaft 4012 of humeral stem 4002 has three ridges and three grooves, although any number of ridges and grooves may be present. The illustrated arrangement of three ridges and three grooves gives the distal shaft 4012 a cross-sectional shape that may be described as tri-lobed, triangular, or Y-shaped. A medial ridge 4016 and two oblique-lateral ridges 4017 are shown; there is an antero-lateral ridge and a postero-lateral ridge. Each ridge 4016, 4017 has a rectangular cross-sectional profile which may have its longest dimension oriented radially outwardly relative to the centerline 4032. Similar to humeral stem 1202, the medial ridge 4016 may include a superimposed longitudinal groove 4058. Holes 4060 may extend through the ridges 4016, 4017 near the proximal body 4010. Sutures, cables, or other lines may be routed through the holes 4060 to re-attach soft tissues or bone fragments to the humerus A lateral groove 4018 and two oblique-medial grooves 4019 are shown; there is an antero-medial groove and a postero-medial groove. The ridges 4016, 4017 may merge together along some or all of the length of the distal shaft 4012 to form a central longitudinal solid portion 4020. The solid portion 4020 may track along, or may define, a longitudinal centerline 4032. The centerline 4032 may be straight or linear, or it may be curved, bent, irregular, and so on. Referring to FIG. 24E, at least the distal portion of the centerline 4032 may be straight or linear in a posterior (or anterior) view. Referring to FIGS. 24D and 24F, the entire centerline 4032 may be straight or linear in medial or lateral views.

Like humeral stem 402, each ridge 4016, 4017 may extend transversely away from the centerline 4032 a first distance near the proximal body 4010 and a second distance farther from the proximal body (closer to the free end). For each ridge 4016, 4017 the second distance may be less than the first distance. The ridges 4016, 4017 and/or grooves 4018, 4019 may also be wider near the proximal end 10 of the distal shaft 4012 and narrower near the distal end 12. The proximal and distal distances and/or the proximal and distal transverse widths for each ridge 4016, 4017 may be the same as, or different from, the corresponding proximal and distal distances of the other ridges of the distal shaft 4012. In the example shown, with three ridges 4016, 4017, there may be three unique proximal distances, three unique distal distances, three unique proximal transverse widths, and/or three unique distal transverse widths. In the example shown, the antero-lateral and postero-lateral ridges 4017 are identical mirror images of each other, while the medial ridge 4016 is different from the ridges 4017. The differences are more pronounced near the proximal body 4010. Optionally, the distal distances may be equal and/or the distal widths may be equal.

Referring to FIG. 24E, humeral stem 4002 illustrates that any humeral stem disclosed herein may include one or more regions with specialized surface structure, and/or one or more different types of surface structure. A first surface structure region 4062 is on the exterior of the proximal body 4010, in other words, proximal to dashed line 4064. A second surface structure region 4066 is on the proximal end of the distal stem 4012, in other words, between dashed lines 4064, 4068. Preferably, the first surface structure region 4062 includes a rough structure suitable to provide initial stability when the proximal body 4010 is impacted into a prepared bone socket, and the second surface structure region 4066 includes a surface structure conducive to bone ongrowth or ingrowth for long-term fixation. The location and extent of the first and second surface structure regions 4062, 4066 may be specified so as to achieve particular short- and long-term fixation objectives.

Figure 25A:
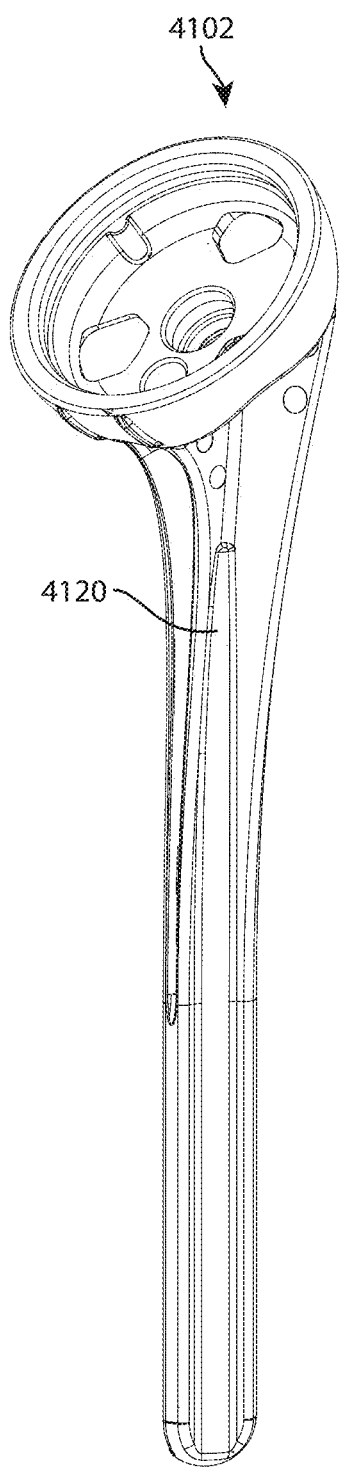
FIG. 25A is an oblique view of yet another humeral stem.
Figure 25B:
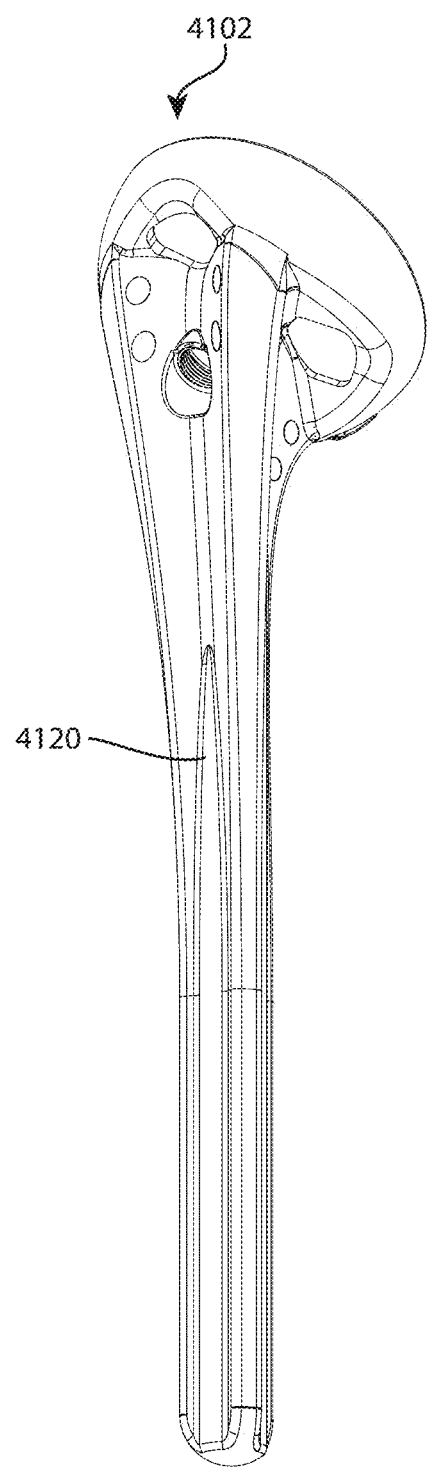
FIG. 25B is another oblique view of the humeral stem of FIG. 25A.

Referring to FIGS. 25A-B, a humeral stem 4102 may be thought of as a variant of humeral stem 4002, in which the solid portion 4120 is thicker than solid portion 4020.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A humeral implant system for implantation in a metaphysis of a humeral bone, the humeral implant system comprising a stem component that comprises:
    a body portion comprising:
        an exterior surface, wherein the exterior surface of the body portion comprises a convex hemispherical shape portion;
        a proximal rim; and an interior socket circumscribed by the proximal rim, wherein no portion of the interior socket extends into a plane defined by the proximal rim, and wherein the interior socket is configured to receive either of a concave humeral articular component and a convex humeral articular component therein; and a shaft portion extending outwardly from the exterior surface of the body portion along a longitudinal shaft centerline, wherein the shaft portion comprises at least three longitudinal ridges arranged around the longitudinal shaft centerline, wherein each longitudinal ridge extends radially away from the longitudinal shaft centerline a first distance near the body portion and a second distance farther from the body portion, wherein the second distance is less than the first distance.

2. The humeral implant system of claim 1, wherein the interior socket comprises a plurality of noncircular holes arranged around a center of the interior socket and extending through the body portion.

3. The humeral implant system of claim 1, wherein the interior socket comprises a central hole in a bottom surface of the interior socket and extending through the body portion.

4. The humeral implant system of claim 1, wherein the shaft portion comprises a cross-sectional shape comprising a Y-shape.

5. The humeral implant system of claim 1, wherein each longitudinal ridge comprises a first transverse width near the body portion and a second transverse width farther from the body portion, wherein the second transverse width is less than the first transverse width.

6. The humeral implant system of claim 1, wherein each longitudinal ridge is separate from the other longitudinal ridges near the body portion, wherein the longitudinal ridges merge together farther from the body portion.

7. The humeral implant system of claim 1, further comprising at least one of the concave humeral articular component and the convex humeral articular component.

8. The humeral implant system of claim 7, further comprising the concave humeral articular component and the convex humeral articular component.

9. The humeral implant system of claim 1, wherein the shaft portion is integrally formed with the body portion.

10. A humeral implant assembly comprising:
a first humeral articular component comprising a first articular surface, the first articular surface comprising a first hemispherical shape portion having a concave shape;
a second humeral articular component comprising a second articular surface, the second articular surface comprising a second hemispherical shape portion having a convex shape; and
a stem component couplable with the humeral articular component and configured for implantation in at least a metaphysis of a[[ long]] humeral bone, the stem component comprising:
a body portion comprising:
an exterior surface, wherein the exterior surface of the body portion comprises a third convex hemispherical shape portion;
a proximal rim; and
an interior socket circumscribed by the proximal rim and shaped to receive the humeral articular component therein, wherein no portion of the interior socket extends into a plane defined by the proximal rim; and a shaft portion integrally formed with the body portion and extending outwardly from the exterior surface of the body portion along a longitudinal shaft centerline, wherein the shaft portion comprises a cross-sectional shape comprising at least three lobes, wherein each lobe extends radially away from the longitudinal shaft centerline, wherein the shaft portion comprises a first cross-sectional overall outer diameter near the body portion and a second cross-sectional overall outer diameter farther from the body portion, wherein the second cross-sectional overall outer diameter is less than the first cross-sectional overall outer diameter.

11. The humeral implant assembly of claim 10, wherein the interior socket comprises a plurality of noncircular holes arranged around a center of the interior socket and extending through the body portion.

12. The humeral implant assembly of claim 10, wherein the interior socket comprises a central hole in a bottom surface of the interior socket and extending through the body portion.

13. The humeral implant assembly of claim 10, wherein the shaft portion comprises a cross-sectional shape comprising a Y-shape.

14. The humeral implant assembly of claim 10, wherein each lobe comprises a first transverse width near the body portion and a second transverse width farther from the body portion, wherein the second transverse width is less than the first transverse width.

15. A humeral implant system for implantation in a metaphysis of a humeral bone, the humeral implant system comprising a stem component that comprises:
a body portion comprising:
an exterior, wherein the exterior comprises a portion of a sphere;
a proximal rim; and
an interior socket circumscribed by the proximal rim, wherein an entirety of the interior socket is recessed below the proximal rim, and wherein the interior socket is configured to receive either of a concave humeral articular component and a convex humeral articular component therein; and
a shaft portion extending outwardly from the exterior of the body portion along a longitudinal shaft centerline, wherein the shaft portion comprises at least three longitudinal columns arranged around the longitudinal shaft centerline, wherein each longitudinal column is separate from the remaining longitudinal columns near the body portion, wherein the longitudinal columns merge together farther from the body portion.

16. The humeral implant system of claim 15, wherein the interior socket comprises a plurality of noncircular holes arranged around a center of the interior socket and extending through the body portion.

17. The humeral implant system of claim 15, wherein the interior socket comprises a central hole in a bottom surface of the interior socket and extending through the body portion.

18. The humeral implant system of claim 15, wherein the interior socket comprises a hole extending through the body portion, wherein the stem component comprises a cavity near the body portion, wherein the cavity is surrounded by the longitudinal columns, wherein the hole and the cavity are open to each other.

19. The humeral implant system of claim 15, wherein the shaft portion comprises a first cross-sectional overall outer diameter near the body portion and a second cross-sectional overall outer diameter farther from the body portion, wherein the second cross-sectional overall outer diameter is less than the first cross-sectional overall outer diameter.

20. The humeral implant system of claim 15, wherein each longitudinal column comprises a first transverse width near the body portion and a second transverse width farther from the body portion, wherein the second transverse width is less than the first transverse width.

21. The humeral implant system of claim 15, wherein at least one of the at least three longitudinal columns comprises a superimposed longitudinal groove formed therein, and wherein the superimposed longitudinal groove comprises a concave surface extending along the at least one of the at least three longitudinal columns.

22. The humeral implant system of claim 15, further comprising at least one of the concave humeral articular component and the convex humeral articular component.

23. The humeral implant system of claim 22, further comprising the concave humeral articular component and the convex humeral articular component.

24. The humeral implant system of claim 15, wherein the shaft portion is integrally formed with the body portion.

\* \* \* \* \*